US009724216B2

(12) United States Patent
Dorn et al.

(10) Patent No.: US 9,724,216 B2
(45) Date of Patent: Aug. 8, 2017

(54) STENT DEVICE DELIVERY SYSTEM WITH INWARDLY TAPERING STENT BED

(75) Inventors: Jurgen Dorn, Neulussheim (DE); Daniel Dietrich, Karlsruhe (DE); Markus Forster, Kandel-Mindelslachen (DE); Jeldrik zum Gahr, Karlsruhe (DE)

(73) Assignee: C. R. Bard, Inc., Murray Hill, NJ (US)

(*) Notice: Subject to any disclaimer, the term of this patent is extended or adjusted under 35 U.S.C. 154(b) by 550 days.

(21) Appl. No.: 12/958,089

(22) Filed: Dec. 1, 2010

(65) Prior Publication Data

US 2011/0137396 A1 Jun. 9, 2011

Related U.S. Application Data

(60) Provisional application No. 61/266,299, filed on Dec. 3, 2009.

(30) Foreign Application Priority Data

Dec. 3, 2009 (GB) .................................. 0921238.2

(51) Int. Cl.
*A61F 2/966* (2013.01)
*A61F 2/95* (2013.01)

(52) U.S. Cl.
CPC ................ *A61F 2/95* (2013.01); *A61F 2/966* (2013.01); *A61F 2002/9665* (2013.01)

(58) Field of Classification Search
CPC .................................. A61F 2/95–2/97; A61F 2002/9505–2002/9665;

(Continued)

(56) References Cited

U.S. PATENT DOCUMENTS

| | | | |
|---|---|---|---|
| 3,953,566 | A | 4/1976 | Gore |
| 3,962,153 | A | 6/1976 | Gore |

(Continued)

FOREIGN PATENT DOCUMENTS

| | | | |
|---|---|---|---|
| DE | 10339628 | A1 | 3/2005 |
| EP | 0732087 | A1 | 9/1996 |

(Continued)

OTHER PUBLICATIONS

EP 0815339.7 filed Aug. 21, 2008 Search Report dated Dec. 22, 2008.

(Continued)

*Primary Examiner* — Darwin Erezo
*Assistant Examiner* — Jonathan Hollm
(74) *Attorney, Agent, or Firm* — C. R. Bard Intellectual Property Buchalter

(57) ABSTRACT

A stent device delivery system and method of making. The stent device delivery system includes a stent device, an outer sheath overlaying the stent device in a radially compact, delivery configuration of the stent device, and an inner catheter extending axially and radially within a lumen of the stent device. The inner catheter provides a stent bed upon which the stent device is located so that a radially inner surface of the stent device engages a radially outer surface of the stent bed. The stent bed may define an inwardly tapering profile, narrowing in radius from a distal portion of the stent device to a proximal portion of the stent device.

15 Claims, 4 Drawing Sheets

(58) Field of Classification Search
CPC ...................... A61M 25/0043–25/0053; A61M 2025/0046–2025/0048
USPC ...................... 606/108; 623/1.11, 1.12, 2.11
See application file for complete search history.

(56) References Cited

U.S. PATENT DOCUMENTS

| | | | | |
|---|---|---|---|---|
| 4,187,390 | A | 2/1980 | Gore | |
| 4,636,162 | A | 1/1987 | Pavy et al. | |
| 4,732,152 | A * | 3/1988 | Wallsten et al. | 623/1.11 |
| 5,087,394 | A | 2/1992 | Keith | |
| 5,217,482 | A | 6/1993 | Keith | |
| 5,324,261 | A | 6/1994 | Amundson et al. | |
| 5,453,090 | A | 9/1995 | Martinez et al. | |
| 5,573,520 | A | 11/1996 | Schwartz et al. | |
| 5,626,605 | A | 5/1997 | Irie et al. | |
| 5,647,857 | A | 7/1997 | Anderson et al. | |
| 5,662,703 | A * | 9/1997 | Yurek et al. | 623/1.12 |
| 5,690,644 | A * | 11/1997 | Yurek et al. | 623/1.11 |
| 5,709,703 | A | 1/1998 | Lukic et al. | |
| 5,718,861 | A | 2/1998 | Andrews et al. | |
| 5,755,769 | A | 5/1998 | Richard et al. | |
| 5,765,682 | A | 6/1998 | Bley et al. | |
| 5,807,520 | A | 9/1998 | Wang et al. | |
| 5,823,995 | A | 10/1998 | Fitzmaurice et al. | |
| 5,824,041 | A * | 10/1998 | Lenker et al. | 606/195 |
| 5,833,694 | A | 11/1998 | Poncet | |
| 5,843,027 | A | 12/1998 | Stone et al. | |
| 5,925,061 | A | 7/1999 | Ogi et al. | |
| 5,968,069 | A * | 10/1999 | Dusbabek et al. | 606/194 |
| 5,992,000 | A | 11/1999 | Humphrey et al. | |
| 6,027,510 | A * | 2/2000 | Alt | 606/108 |
| 6,063,092 | A | 5/2000 | Shin | |
| 6,126,685 | A | 10/2000 | Lenker et al. | |
| 6,149,681 | A | 11/2000 | Houser et al. | |
| 6,168,748 | B1 | 1/2001 | Wang et al. | |
| 6,224,803 | B1 | 5/2001 | Tiernan | |
| 6,254,628 | B1 | 7/2001 | Wallace et al. | |
| 6,309,383 | B1 | 10/2001 | Campbell et al. | |
| 6,368,344 | B1 | 4/2002 | Fitz | |
| 6,425,898 | B1 * | 7/2002 | Wilson et al. | 606/108 |
| 6,447,540 | B1 | 9/2002 | Fontaine et al. | |
| 6,613,067 | B1 | 9/2003 | Johnson | |
| 6,613,075 | B1 | 9/2003 | Healy et al. | |
| 6,629,992 | B2 | 10/2003 | Bigus et al. | |
| 6,645,238 | B2 | 11/2003 | Smith | |
| 6,702,843 | B1 | 3/2004 | Brown et al. | |
| 6,805,703 | B2 | 10/2004 | McMorrow | |
| 6,833,002 | B2 | 12/2004 | Stack et al. | |
| 6,837,870 | B2 | 1/2005 | Dunchamp | |
| 6,841,029 | B2 * | 1/2005 | Lim | 156/308.6 |
| 6,946,092 | B1 | 9/2005 | Bertolino et al. | |
| 7,604,668 | B2 | 10/2009 | Farnsworth | |
| 7,815,669 | B2 | 10/2010 | Matsuoka et al. | |
| 7,993,350 | B2 | 8/2011 | Ventura | |
| 8,568,467 | B2 | 10/2013 | Dorn et al. | |
| 2001/0011180 | A1 | 8/2001 | Fitzmaurice et al. | |
| 2001/0027323 | A1 * | 10/2001 | Sullivan et al. | 606/108 |
| 2002/0016597 | A1 | 2/2002 | Dwyer et al. | |
| 2002/0099431 | A1 | 7/2002 | Armstrong et al. | |
| 2002/0180107 | A1 | 12/2002 | Jackson et al. | |
| 2003/0083730 | A1 | 5/2003 | Stinson | |
| 2003/0093106 | A1 * | 5/2003 | Brady | A61F 2/013 606/194 |
| 2003/0109886 | A1 | 6/2003 | Keegan et al. | |
| 2003/0114912 | A1 | 6/2003 | Sequin et al. | |
| 2003/0125709 | A1 | 7/2003 | Eidenschink | |
| 2003/0125791 | A1 * | 7/2003 | Sequin et al. | 623/1.11 |
| 2003/0139801 | A1 | 7/2003 | Sirhan et al. | |
| 2003/0163193 | A1 * | 8/2003 | Widenhouse | 623/1.12 |
| 2003/0204235 | A1 | 10/2003 | Edens et al. | |
| 2004/0064130 | A1 | 4/2004 | Carter | |
| 2004/0143272 | A1 | 7/2004 | Cully et al. | |
| 2004/0143286 | A1 | 7/2004 | Johnson et al. | |
| 2004/0143315 | A1 | 7/2004 | Bruun et al. | |
| 2004/0148007 | A1 | 7/2004 | Jackson et al. | |
| 2004/0199239 | A1 | 10/2004 | Austin et al. | |
| 2004/0267346 | A1 * | 12/2004 | Shelso | 623/1.11 |
| 2005/0004555 | A1 | 1/2005 | Pursley | |
| 2005/0049667 | A1 | 3/2005 | Arbefeuille et al. | |
| 2005/0113902 | A1 | 5/2005 | Geiser et al. | |
| 2005/0240254 | A1 | 10/2005 | Austin | |
| 2006/0015171 | A1 | 1/2006 | Armstrong | |
| 2006/0030923 | A1 | 2/2006 | Gunderson | |
| 2006/0089627 | A1 | 4/2006 | Burnett et al. | |
| 2006/0100687 | A1 | 5/2006 | Fahey et al. | |
| 2006/0142838 | A1 | 6/2006 | Molaei et al. | |
| 2006/0200221 | A1 * | 9/2006 | Malewicz | A61F 2/966 623/1.11 |
| 2006/0212105 | A1 | 9/2006 | Dorn et al. | |
| 2006/0247661 | A1 | 11/2006 | Richards et al. | |
| 2006/0259124 | A1 | 11/2006 | Matsuoka et al. | |
| 2007/0050017 | A1 | 3/2007 | Sims et al. | |
| 2007/0055338 | A1 | 3/2007 | Dorn | |
| 2007/0074805 | A1 * | 4/2007 | Leeflang et al. | 156/84 |
| 2008/0118546 | A1 * | 5/2008 | Thatcher et al. | 424/426 |
| 2008/0243224 | A1 | 10/2008 | Wallace et al. | |
| 2009/0125093 | A1 | 5/2009 | Hansen | |
| 2009/0204196 | A1 | 8/2009 | Weber | |
| 2009/0254169 | A1 | 10/2009 | Spenser et al. | |
| 2009/0312828 | A1 * | 12/2009 | Vrba | 623/1.11 |
| 2009/0312831 | A1 | 12/2009 | Dorn | |
| 2010/0049297 | A1 | 2/2010 | Dorn | |
| 2010/0168835 | A1 | 7/2010 | Dorn | |
| 2010/0249907 | A1 | 9/2010 | Dorn et al. | |
| 2011/0060397 | A1 | 3/2011 | Dorn | |
| 2011/0137396 | A1 | 6/2011 | Dorn et al. | |
| 2011/0137400 | A1 | 6/2011 | Dorn et al. | |
| 2011/0137401 | A1 | 6/2011 | Dorn et al. | |
| 2011/0137402 | A1 | 6/2011 | Dorn et al. | |
| 2012/0059448 | A1 | 3/2012 | Parker et al. | |
| 2012/0083869 | A1 * | 4/2012 | Wubbeling | A61F 2/966 623/1.11 |
| 2012/0143303 | A1 | 6/2012 | Dorn et al. | |

FOREIGN PATENT DOCUMENTS

| | | | |
|---|---|---|---|
| EP | 0941713 | A1 | 9/1999 |
| EP | 1062966 | A1 | 12/2000 |
| EP | 0732087 | B1 | 6/2003 |
| EP | 1679095 | A1 | 7/2006 |
| FR | 2688688 | A1 | 9/1993 |
| JP | S59-51863 | A | 3/1984 |
| JP | H09-512194 | A | 12/1997 |
| JP | 2000-116788 | A | 4/2000 |
| JP | 2001-9037 | | 1/2001 |
| JP | 2001-299926 | A | 10/2001 |
| JP | 2006-515786 | A | 6/2006 |
| WO | 8603398 | A1 | 6/1986 |
| WO | 9317636 | A1 | 9/1993 |
| WO | 9415549 | A1 | 7/1994 |
| WO | 9530385 | A1 | 11/1995 |
| WO | 9632078 | A1 | 10/1996 |
| WO | 9820812 | A1 | 5/1998 |
| WO | 0018329 | A1 | 4/2000 |
| WO | 0108599 | A1 | 2/2001 |
| WO | 02/38084 | A2 | 5/2002 |
| WO | 0238084 | | 5/2002 |
| WO | 03002019 | A2 | 1/2003 |
| WO | 03002034 | A2 | 1/2003 |
| WO | 2004062458 | A2 | 7/2004 |
| WO | 2004066809 | A2 | 8/2004 |
| WO | 2004096091 | A1 | 11/2004 |
| WO | 2005072650 | A1 | 8/2005 |
| WO | 2006019626 | A2 | 2/2006 |
| WO | 2006020028 | A1 | 2/2006 |
| WO | 2006071245 | A1 | 7/2006 |
| WO | 2006086709 | A1 | 8/2006 |
| WO | 2006096229 | A1 | 9/2006 |
| WO | 2006130326 | A2 | 12/2006 |
| WO | 2007103666 | A2 | 9/2007 |
| WO | 2009050265 | A1 | 4/2009 |
| WO | 2009135934 | A1 | 11/2009 |
| WO | 2010076052 | A1 | 7/2010 |

(56) References Cited

FOREIGN PATENT DOCUMENTS

| | | | |
|---|---|---|---|
| WO | 2010076057 | A1 | 7/2010 |
| WO | 2010115925 | A1 | 10/2010 |
| WO | 2011067277 | A1 | 6/2011 |
| WO | 2011067280 | A1 | 6/2011 |
| WO | 2012072729 | A1 | 6/2012 |

OTHER PUBLICATIONS

EP 12164925.5 filed Jul. 6, 2011 Extended European Search Report dated Jul. 26, 2012.
PCT/EP2009/055592 filed May 8, 2009 International Preliminary Report on Patentability dated Nov. 9, 2010.
PCT/EP2009/055592 filed May 8, 2009 Search Report dated Aug. 3, 2009.
PCT/EP2009/055592 filed May 8, 2009 Written Opinion dated Aug. 3, 2009.
PCT/EP2009/060827 filed Aug. 21, 2009 Preliminary Report on Patentability dated Oct. 19, 2010.
PCT/EP2009/060827 filed Aug. 21, 2009 Search Report dated Nov. 16, 2009.
PCT/EP2009/060827 filed Aug. 21, 2009 Written Opinion dated Nov. 16, 2009.
PCT/EP2009/064057 filed Oct. 26, 2009 International Preliminary Report on Patentability dated Jun. 6, 2011.
PCT/EP2009/064057 filed Oct. 26, 2009 International Search Report dated May 17, 2010.
PCT/EP2009/064057 filed Oct. 26, 2009 Written Opinion dated May 17, 2010.
PCT/EP2010/068620 filed Dec. 1, 2010 International Preliminary Report on Patentability dated Aug. 5, 2011.
PCT/EP2010/068620 filed Dec. 1, 2010 International Search Report dated Apr. 21, 2011.
PCT/EP2010/068620 filed Dec. 1, 2010 Written Opinion dated Apr. 21, 2011.
PCT/EP2010/068627 filed Dec. 1, 2010 International Preliminary Report on Patentability dated Jul. 20, 2011.
PCT/EP2010/068627 filed Dec. 1, 2010 International Search Report dated Apr. 21, 2011.
PCT/EP2010/068627 filed Dec. 1, 2010 Written Opinion dated Apr. 21, 2011.
PCT/EP2011/071489 filed Dec. 1, 2011 International Search Report dated Mar. 6, 2012.
U.S. Appl. No. 12/545,409, filed Aug. 21, 2009 Non-Final Office Action dated Apr. 13, 2012.
U.S. Appl. No. 12/650,863, filed Dec. 31, 2009 Non-Final Office Action dated Jun. 8, 2012.
U.S. Appl. No. 12/991,112, filed Nov. 4, 2010 Non-Final Office Action dated Apr. 3, 2012.
PCT/EP2008/064036 filed Oct. 17, 2008 International Preliminary Examination Report dated Apr. 20, 2010.
PCT/EP2008/064036 filed Oct. 17, 2008 Search Report dated Jan. 22, 2009.
PCT/EP2008/064036 filed Oct. 17, 2008 Written Opinion dated Jan. 22, 2009.
U.S. Appl. No. 12/545,409, filed Aug. 21, 2009 Non-Final Office Action dated Apr. 29, 2013.
U.S. Appl. No. 12/650,863, filed Dec. 31, 2009 Advisory Action dated Dec. 31, 2012.
U.S. Appl. No. 12/650,863, filed Dec. 31, 2009 Final Office Action dated Oct. 11, 2012.
U.S. Appl. No. 12/738,568, filed Apr. 16, 2010 Final Office Action dated Mar. 29, 2013.
U.S. Appl. No. 12/738,568, filed Apr. 16, 2010 Non-Final Office Action dated Nov. 2, 2012.
U.S. Appl. No. 12/958,123, filed Dec. 1, 2010 Non-Final Office Action dated Mar. 25, 2013.
U.S. Appl. No. 12/958,184, filed Dec. 1, 2010 Non-Final Office Action dated Mar. 14, 2013.
U.S. Appl. No. 12/958,220, filed Dec. 1, 2010 Non-Final Office Action dated Mar. 15, 2013.
U.S. Appl. No. 12/991,112, filed Nov. 4, 2010 Final Office Action dated May 9, 2013.
U.S. Appl. No. 13/309,420, filed Dec. 1, 2011 Non-Final Office Action dated Apr. 15, 2013.
JP 2011-523429 Office Action dated Jul. 17, 2013.
U.S. Appl. No. 12/738,568, filed Apr. 16, 2010 Advisory Action dated Jun. 10, 2013.
U.S. Appl. No. 12/958,123, filed Dec. 1, 2010 Advisory Action dated Oct. 17, 2013.
U.S. Appl. No. 12/958,184, filed Dec. 1, 2010 Advisory Action dated Nov. 5, 2013.
U.S. Appl. No. 12/958,184, filed Dec. 1, 2010 Final Office Action dated Aug. 14, 2013.
U.S. Appl. No. 12/958,220, filed Dec. 1, 2010 Advisory Action dated Nov. 5, 2013.
U.S. Appl. No. 12/958,220, filed Dec. 1, 2010 Final Office Action dated Aug. 13, 2013.
JP 2011-542735 Office Action dated Jan. 6, 2014.
PCT/EP2009/060827 filed Aug. 21, 2009 International Search Report dated Nov. 16, 2009.
U.S. Appl. No. 12/545,409, filed Aug. 21, 2009 Final Office Action dated Feb. 12, 2015.
U.S. Appl. No. 12/545,409, filed Aug. 21, 2009 Final Office Action dated Nov. 20, 2013.
U.S. Appl. No. 12/545,409, filed Aug. 21, 2009 Non-Final Office Action dated Aug. 6, 2015.
U.S. Appl. No. 12/545,409, filed Aug. 21, 2009 Non-Final Office Action dated Mar. 20, 2014.
U.S. Appl. No. 12/545,409, filed Aug. 21, 2009 Pre-Brief Conference Decision dated Jun. 1, 2015.
U.S. Appl. No. 12/650,863, filed Dec. 31, 2009 Final Office Action dated Jul. 28, 2015.
U.S. Appl. No. 12/650,863, filed Dec. 31, 2009 Non-Final Office Action dated Jan. 7, 2015.
U.S. Appl. No. 12/958,123, filed Dec. 1, 2010 Advisory Action dated Feb. 10, 2015.
U.S. Appl. No. 12/958,123, filed Dec. 1, 2010 Final Office Action dated Nov. 19, 2014.
U.S. Appl. No. 12/958,123, filed Dec. 1, 2010 Non-Final Office Action dated Aug. 19, 2015.
U.S. Appl. No. 12/958,123, filed Dec. 1, 2010 Non-Final Office Action dated Jun. 11, 2014.
U.S. Appl. No. 12/958,184, filed Dec. 1, 2010 Advisory Action dated May 18, 2015.
U.S. Appl. No. 12/958,184, filed Dec. 1, 2010 Final Office Action dated Feb. 10, 2015.
U.S. Appl. No. 12/958,184, filed Dec. 1, 2010 Non-Final Office Action date Aug. 10, 2015.
U.S. Appl. No. 12/958,184, filed Dec. 1, 2010 Non-Final Office Action dated Aug. 5, 2014.
U.S. Appl. No. 12/958,220, filed Dec. 1, 2010 Final Office Action dated Oct. 23, 2014.
U.S. Appl. No. 12/958,220, filed Dec. 1, 2010 Non-Final Office Action dated Apr. 9, 2014.
U.S. Appl. No. 12/958,220, filed Dec. 1, 2010 Non-Final Office Action dated Jul. 21, 2015.
U.S. Appl. No. 12/991,112, filed Nov. 4, 2010 Advisory Action dated Dec. 23, 2014.
U.S. Appl. No. 12/991,112, filed Nov. 4, 2010 Final Office Action dated Sep. 11, 2014.
U.S. Appl. No. 12/991,112, filed Nov. 4, 2010 Non-Final Office Action dated Mar. 21, 2014.
U.S. Appl. No. 13/309,420, filed Dec. 1, 2011 Advisory Action dated Feb. 13, 2014.
U.S. Appl. No. 13/309,420, filed Dec. 1, 2011 Final Office Action dated Feb. 24, 2015.
U.S. Appl. No. 13/309,420, filed Dec. 1, 2011 Final Office Action dated Nov. 8, 2013.
U.S. Appl. No. 13/309,420, filed Dec. 1, 2011 Non-Final Office Action dated Aug. 19, 2014.

(56) References Cited

OTHER PUBLICATIONS

U.S. Appl. No. 13/309,420, filed Dec. 1, 2011 Notice of Allowance dated Jul. 9, 2015.

* cited by examiner 1
2
3
4
5
6
7
8
9
10
11
12
13
14
15
16

STENT DEVICE DELIVERY SYSTEM WITH INWARDLY TAPERING STENT BED

PRIORITY

This application claims the priority benefit of U.S. Provisional Application No. 61/266,299, filed Dec. 3, 2009, and U.K. Patent Application No. 0921238.2, filed Dec. 3, 2009, each of which is incorporated by reference in its entirety into this application.

FIELD OF THE INVENTION

The present invention relates to a stent device delivery system comprising a stent device and an outer sheath overlaying the stent device. The outer sheath is axially retractable relative to the stent device in order to deploy the stent device. The present invention also relates to a method of making the stent device delivery system.

BACKGROUND

Stent device delivery systems are known in the art. The purpose of such a system is to deliver a stent device to a diseased vascular lumen. The stent device provides a support structure against collapse of the diseased vascular lumen. There are at least two types of stent device delivery systems that are of relevance to the present invention.

A first type provides a rolling outer sheath for deploying a stent device. Such a "rolling" outer sheath system is disclosed, for example, in U.S. Pat. No. 6,544,278, which is incorporated by reference in its entirety into this application. The outer sheath is made from a tubular sleeve that is folded back upon itself in order to define an inner layer, an outer layer and a fold-over portion connecting the inner layer and the outer layer. The inner layer and the outer layer overlay the stent device in a delivery configuration of the stent device. The outer layer is axially movable relative to the inner layer in a proximal direction, which causes the fold-over portion to move axially from a distal end to a proximal end of the stent device in a rolling manner, thereby retracting the outer sheath from the stent device. The stent device, unconstrained by the outer sheath, is able to radially expand into an operative configuration for supporting the diseased vascular lumen.

A second type of prior art delivery system provides an outer sheath that slides, rather than rolls, over the stent device in retracting the outer sheath from the stent device. Such a delivery system is disclosed in, for example WO 2006/133959, which is incorporated by reference in its entirety into this application. In this "pullback" outer sheath system, a proximal end of the outer sheath is pulled upon in order to drag the outer sheath axially from the stent device.

In terms of deployment force, rolling outer sheath delivery systems are advantageous in some circumstances as compared to pullback outer sheath delivery systems. In pullback outer sheath delivery systems, friction between the outer surface of the stent device and the inner surface of the outer sheath has to be overcome in order to move the outer sheath relative to the stent device. The longer the stent device, the greater the friction that has to be overcome. This puts certain constraints on what materials can be used for the outer sheath because of strength issues. Rollback outer sheath delivery systems are not as constrained by high frictional force considerations, but deployment force can still be a problem as, during rollback, the fold-over portion must generally slide against a more proximal portion of the inner layer. However, two-layer rollback constructions can disadvantageously increase the cross-sectional profile of the stent relative to single-layer pullback construction. In order to allow for a rolling outer sheath delivery system of comparable profile to a pullback system, the outer sheath is made of thinner, and thus weaker, materials than an equivalent pullback outer sheath delivery system. However, if the friction during rollback exceeds the strength of the materials used, reliability of the rolling outer sheath stent delivery system may be jeopardized.

In both the pullback outer sheath delivery stent device delivery systems and the rolling outer sheath stent device delivery systems, a pull member is used to apply a pulling force to retract the outer sheath from the stent device. The pull member may extend from a handle portion to a position just proximal of the stent device where it is attached to the outer sheath. One way to attach a pull member to an outer sheath is disclosed in WO 2006/133959, which is referred to above. In this document, outer and inner bands are arranged with the outer sheath compressed between them. A pull wire or pull member is brazed to the inner band and runs all the way back to a handle portion of the stent device delivery system. A strong and reliable connection between the pull member and the outer sheath is essential for successful deployment of the stent device by retracting the outer sheath. It is desirable to provide an alternative manner of strongly attaching the pull member to the outer sheath, while also retaining a low profile configuration.

Accordingly, in one embodiment, provided is a stent device delivery system that is reliable in terms of deployment of the stent device by retracting the outer sheath and is low profile for ease of delivery of the stent device to the diseased vascular lumen site. In one embodiment, provided is a method of making such a stent device delivery system. Other advantages of features of the present invention will become apparent to the skilled reader from the following description of embodiments of the invention.

SUMMARY

In one aspect, the present invention provides a stent device delivery system comprising a stent device and an outer sheath overlaying the stent device in a radially compact delivery configuration of the stent device. The outer sheath is retractable relative to the stent device in order to allow radial expansion of the stent device to a deployed configuration of the stent device. The outer sheath comprises a first layer of polymeric material (or plastic layer) and a reinforcement layer of polymeric material (or reinforcement plastic layer) that are laminated together. In a preferred embodiment, the first layer and the reinforcement layer are glued together by a glue layer radially between the first layer and the reinforcement layer.

The first aspect of the present invention allows the outer sheath to be made of plastic layers, which allow the outer sheath to be made relatively thin as compared to some prior art outer sheaths. Suitable plastic materials for the outer sheath, as many polymers, are generally neckable under tension from a pull element which would cause the outer sheath to reduce in diameter. This reduction in diameter may result in an increased radial compression on inner components of the system resulting in an increased deployment force. This, if beyond a maximum allowable threshold for the sheath, could give rise to deployment failure. The reinforcement plastic layer of the first aspect of the present invention strengthens the first plastic layer, while the preferred presence of the glue layer has been found to strongly inhibit necking of the first plastic layer and the reinforcement plastic layer, as glues typically are not substantially ductile when set or cured. This combination of layers has been surprisingly found to offer a thin outer sheath that reliably deploys without undue increase in deployment force.

Preferably, the first layer, the reinforcement layer and, where present, the preferred glue layer overlay, and thus extend along, the stent device. Necking of the outer sheath in the region of the stent device would particularly present a barrier to successful retraction of the outer sheath from the stent device.

In another preferred embodiment, the outer sheath comprises a distal portion overlaying the stent device and a transition portion proximal of the stent device, wherein the transition portion tapers in a proximal direction. Preferably, a portion of the outer sheath proximal of the transition portion includes the first layer, the reinforcement layer and preferably, the glue layer of the outer sheath. Preferably, the tapering portion includes the first layer, the preferred glue layer and the reinforcement layer. It has been found in practice that the outer sheath is particularly stressed at the transition portion and proximal to the transition portion when being pulled for retraction from the stent device. Accordingly, provision of the reinforcement layer and the preferred glue layer at at least one of these locations is particularly advantageous for the avoidance of failure.

The stent device delivery system preferably further comprises a pull member attached to the outer sheath to be pulled upon in order to retract the outer sheath from the stent device. Preferably, the pull member is embedded and sandwiched between the first layer and the reinforcement layer. Preferably, the pull member is embedded in the glue layer. Embedding the pull member in the glue layer allows uniform transfer of force while providing local strength. This manner of attachment of the pull member to the outer sheath is sufficiently strong for retraction of the outer sheath from the stent device, allows a low profile configuration and is easy to manufacture.

In one preferred embodiment, the preferred glue layer, the pull member, the first layer and the reinforcement layer coextend axially for a distance of at least about 1 inch (3 cm), at least about 2 inches (5 cm) or at least about 3 inches (8 cm). This feature of the first aspect of the present invention ensures a strong attachment of the pull member to the outer sheath.

The above described first reinforcement layer of the outer sheath and the above described attachment of the pull member to the outer sheath are applicable to both a pullback stent device delivery system and a rolling membrane stent device delivery system. In the former system, the first layer is in sliding contact with the stent device and the preferred glue layer and the reinforcement layer overlays the stent device. Pulling on the pull member will cause the first layer, the preferred glue layer and the reinforcement layer to move axially relative to the stent device in conjunction as a single laminar structure. The first layer and the reinforcement layer are integrally formed with one another. That is, the first layer and the second layer are formed from the same tube of material, which has been folded back on itself. Preferably, the pull member overlays the stent device and extends to a distal end of the stent device. This has been found to offer an effective solution for ensuring successful pullback of the outer sheath.

In the latter delivery system, the outer sheath comprises an inner layer, an outer layer and a fold-over portion connecting the inner layer and the outer layer, whereby axial movement of the outer layer relative to the inner layer causes axial movement of the fold-over portion relative to the stent device so that the fold-over portion can be moved proximal of the stent device in order to retract the outer sheath. The outer layer includes the first layer, the preferred glue layer and the reinforcement layer. In a rolling system, necking of the outer layer, and the concomitant increase in radial friction forces, can cause the outer sheath to stick during retraction. Accordingly, it offers deployment reliability to form the outer layer with the first layer, the reinforcement layer and the preferred glue layer. Preferably, the pull member is attached to the outer sheath at the proximal portion of the outer sheath (the portion proximal of the transition portion) discussed above in the rolling stent device delivery system.

The first layer and the reinforcement layer are preferably cold-drawn plastic layers. Such layers are thin, strong and easy to manipulate during manufacturing of the stent device delivery system. Preferably, the plastic is polyethylene terephthalate (PET). This is a particularly useful material for the outer sheath of the first aspect of the present invention. Cold-drawing of the sheath during manufacture with the stent in place permits a reduced profile to be maintained. However, due to the reduced profile, such configurations are particularly susceptible to the necking effect described earlier.

Preferably, the pull member is a pull wire. Preferably, the pull wire is flattened along at least a portion where it is embedded in between the first layer and the reinforcement layer. This ensures both a low profile configuration, an increased surface area for interaction with the layers, and a strong attachment to the outer sheath.

The above described manner of attaching a pull member to an outer sheath of a stent device delivery system is also an independently applicable modification to the prior art. Accordingly, in a second aspect of the present invention there is provided a stent device delivery system comprising a stent device and an outer sheath overlaying the stent device in a radially compact, delivery configuration of the stent device. The outer sheath is retractable relative to the stent device to allow radial expansion of the stent device to a deployed configuration. The outer sheath includes a first layer and a second layer that are laminated together and preferably glued together by a glue layer radially between the first and second layers. A portion of the pull member is attached to the outer sheath by positioning the portion radially between the inner and outer layers of the outer sheath. Preferably, the portion of the pull member is embedded in and glued by the glue layer. This attachment of the pull member to the outer sheath allows a sufficiently strong attachment force, while avoiding measures that necessitate an increase in profile of the delivery system.

In a preferred embodiment, the pull member is positioned radially between the first layer and the second layer of the outer sheath, and preferably embedded in the glue layer, for an axial distance of at least about 1 inch (3 cm), at least about 2 inches (5 cm), or at least about 3 inches (8 cm). A long attachment distance ensures a strong connection of the pull member to the outer sheath.

Preferably, the pull member is a pull wire. The pull wire is preferably flattened at a distal end portion where the portion is embedded between the inner and outer layer. This measure increases the attachment area while maintaining a low profile configuration.

Preferably, the first and second layers are made of a cold-drawn plastic, preferably a cold-drawn polyester material such as cold-drawn PET.

It is a preferred embodiment of the present invention to combine the first and second aspects. Thus, preferably the first layer of the second aspect of the present invention is the first layer of the first aspect of the present invention and the second layer of the second aspect of the present invention is the reinforcement layer of the first aspect of the present invention.

In a third aspect of the present invention, there is provided a stent device delivery system comprising a stent device and an outer sheath overlaying the stent device in a radially compact, delivery configuration of the stent device. The outer sheath is retractable from a distal end of the stent device to a proximal end of the stent device to allow for radial expansion of the stent device to a deployed configuration. An inner catheter extends within a lumen of the stent device and provides a stent bed upon which the stent device is located. The stent bed defines an inwardly tapering profile, narrowing in radius from a distal portion of the stent device to a proximal portion of the stent device.

The tapering profile of the stent bed, it is thought, induces a tapering profile to the stent device, which is radially narrower at the proximal portion than the distal portion of the stent device. Necking typically occurs in an extended interval during retraction. By allowing the proximal portion of the stent to be compressed to a greater extent than the distal portion, as the sheath retracts, the moving distal edge of the outer sheath progressively passes over a radially narrower profile of the stent device. This has consequently been found to reduce deployment force and also inhibits stent device deployment failure.

In a preferred embodiment, the stent bed tapers at a gradient (change in outer diameter of the stent bed divided by axial length over which the change in outside diameter occurs) of 0.0003 to 0.005, preferably 0.0005 to 0.002 and preferably 0.0006 to 0.0009. One way to calculate the gradient is to determine the largest outer diameter of the stent bed which will be at the distal portion of the stent device, and determine the lowest outer diameter of the stent bed, which will be at the proximal portion of the stent device. A linear change from the largest outside diameter to the smallest outside diameter can then be assumed in order to determine the gradient. While in some embodiments, the tapering profile is linear, other embodiments are envisaged, as below, where the change in outer diameter occurs stepwise. One implementation could involve the outer diameter changing by varying extents along the length of the stent device. The gradient is, in essence, an average gradient of the stent bed over the length of the stent device from the distal portion to the proximal portion.

In one embodiment, the stent bed is axially continuous with respect to the stent device. The stent bed thus forms a continuously tapering profile from the distal portion to the proximal portion of the stent device. In another embodiment, the stent bed is formed by a plurality of axially separated portions, such as axially separated band members. In the case of the use of axially separate band members, the bands have a progressively reducing outside diameter in the proximal direction, which preferably involves a stepwise reduction from one band to an adjacent band in the proximal direction, where each band has a constant outside diameter. Alternatively, the bands themselves can have an inwardly tapering outside diameter in the proximal direction. In both the continuous layer and separated band members embodiments, the stent bed may taper in a step wise fashion and there may be 2, 3, 4, 5, 6 or more steps. Thus, there may be 2, 3, 4, 5, 6 or more band members.

As well as, it is thought, inducing a tapering profile on the stent device, the stent bed also has a holding function for axially holding the stent device relative to the inner catheter. The stent bed is preferably made of a compressible material and the stent device is pressed into the stent bed to deform the stent bed. The outer sheath maintains the stent device partially embedded in the stent bed in this way. This partial embedding provides a form fit resisting undesirable axial movement of the stent device relative to the inner catheter. Further, the stent bed is preferably made of a tacky material, which provides a radial as well as an axial holding force on the stent device relative to the inner catheter. During expansion of the stent device, the stent device peels away from the tacky material of the stent bed. The use of both tacky and compressible materials for the stent bed provides a combination of form fit and high strength axial lock to securely position the stent device in an axial direction, which will assist in correct positional deployment at the target diseased vascular lumen site. Suitable materials for the stent bed are rubber, silicone glue or polyether block amide (PEBAX). Another example suitable material is the glue sold under the trade name Dymax. The materials may be sprayed on or coated on in some other way.

The stent bed is preferably formed as a layer on the inner catheter.

Preferably, the stent device delivery system comprises a pull member for putting in endwise tension to retract the outer sheath. The outer sheath preferably comprises a distal portion overlaying the stent device, a proximal portion where the outer sheath is attached to the pull member and a transition portion connecting the distal portion and the proximal portion, where the transition portion tapers inwardly from the distal portion to the proximal portion. Thus, the outer sheath is attached to the pull member at a radially inward position as compared to the outside diameter of the outer sheath at the distal portion overlaying the stent device. In such a pulling configuration, the pulling force is imparted to the outer sheath from a radially inward location. The tapering profile of the stent bed is particularly useful in such configurations for reducing deployment force and increasing deployment reliability.

The tapering profile is particularly useful when applied to a rolling stent device delivering system. Thus, in a preferred embodiment, the outer sheath comprises an inner layer, contacting an outer surface of the stent device, an outer layer and a fold-over portion connecting the inner layer and the outer layer. Proximal movement of the outer layer relative to the inner layer will cause the fold-over portion to move proximally axially relative to the stent device and thus enables retraction of the outer sheath. The tapering profile of the stent bed can yield an ever increasing ease of sliding between the inner layer proximal portion still on the stent device and the outer layer sliding past it proximally to ease any tendency for sticking of the rolling mechanism. It is thought that undulations on the outer surface of the stent device, perhaps in combination with necking of the outer sheath, has, in the past, caused sticking of the rolling mechanism, which increases the deployment force and can cause deployment failure. It is believed that the increased gap provided by the tapering profile alleviates or avoids such difficulties.

The tapering profile is also applicable to a pullback stent device delivery system. In such a system, the outer sheath slides over the stent device from a distal end to a proximal end during retraction as the pull member is put under endwise tension. In one embodiment, the outer sheath comprises a first layer and a second or reinforcement layer that are laminated together, preferably by a glue layer radially between the first and second layers so that the first layer, the preferred glue layer and the second layer are moved axially in conjunction relative to the stent device to retract the outer sheath. Even if the inner layer and the outer layer are made of a neckable plastic material, which can advantageously be made thin, the tapering profile allows a small amount of necking of the outer sheath towards a proximal end of the stent device to not cause sticking of the outer sheath during retraction.

Preferably, the outer sheath is formed having a tapering profile following the tapering profile of the stent bed. "Following" the taper here means tapering in the same direction. Preferably, the outer sheath also tapers at the same gradient as the stent bed. The manner in which this is achieved is described below. Having the outer sheath tapered in this way reinforces the advantages of reducing stent deployment force and increasing stent deployment reliability. Similarly, it is thought, the stent device is preferably forced to share the tapering profile of the stent bed by compression against the tapering stent bed and by the tapering profile of the outer sheath. The outer sheath may be formed having a tapering profile in a region enclosing the stent, or the taper of the outer sheath may extend substantially beyond the region enclosing the stent device.

In one embodiment, the outer sheath is formed by folding a sleeve of material, preferably plastic, back onto itself so as to define the inner layer and the outer layer of the outer sheath in the rolling system described above or the first layer and the second layer in the pull back system described above. Glue can be applied between the first and second layers or the first and second layers can be laminated together to form the pull back stent device delivery system discussed above or the inner and outer layers can be allowed to move relative to one another to provide the rolling stent device delivery system discussed above. Preferably, the sleeve of material is formed into the tapered profile of the outer sheath including the portion of the sleeve that will form the inner or first layer and the portion of the sleeve that will form the outer or second layer. This provides an outer sheath having an inner or first layer tapering inwardly from the distal portion to the proximal portion of the stent device and an outer or second layer that tapers outwardly from the distal portion to the proximal portion of the stent device, thereby further increasing the potential gap between these layers to avoid sticking during retraction of the outer sheath. The outer sheath is preferably made of a cold-drawn plastic material. The cold-drawn plastic material is formed into the tapered profile by cold-drawing over a tapered mandrel as described below.

The features of the first, second and third aspects of the present invention are combinable. Thus, features of the stent device delivery system described with respect to any one of the first to third aspects of the present invention may be combined with the stent device delivery system of any one of the other aspects of the present invention.

In a fourth aspect of the present invention, there is provided a method of making a stent device delivery system. The method comprises a step of loading the stent device into a sleeve of plastic material. The method further comprises a step of positioning an inner catheter into a lumen of the stent device. The inner catheter presents a stent bed for the stent device to be located upon. The stent bed has a tapering profile. The method yet further comprises a step of cold-drawing the sleeve with the stent device loaded therein and located on the stent bed to reduce the diameter of the sleeve, and thus the stent device, to engage the stent device and the stent bed and put the stent device into a reduced profile, delivery configuration. The sleeve provides an outer sheath of the stent device delivery system that is retractable relative to the stent device to allow the stent device to radially expand to a deployed configuration.

Cold-drawing of the outer sheath according to the above method forces the stent device onto the stent bed, which will, it is thought, induce the tapered profile of the stent bed to the stent device. Further, the outer sheath will be cold-drawn to share this tapered profile. The benefits of this tapered profile have been discussed above. Cold-drawing the stent also permits the overall profile of the delivery system to be advantageously reduced by a combination of enhanced stent compression and reduced sheath radial thickness.

The sleeve of plastic material may be folded back onto itself to provide the outer sheath with a first layer, a second, outer layer and a distal fold-over portion connecting the first layer and the second layer. The first layer and the second layer may be laminated together, preferably by a glue layer, in providing a pullback stent device delivery system. Alternatively, the inner layer and the outer layer may be left movable relative to one another to provide a rolling stent device delivery system whereby the first, inner layer and the second, outer layer are able to be moved relative to one another to cause the fold-over portion (rolling edge) to move relative to the stent device thereby allowing retraction of the outer sheath, and the stent to be radially expanded.

The tapering profile of the stent bed tapers inwardly from a distal portion of the stent device to a proximal portion of the stent device. The terms distal and proximal in this instance are to be understood with respect to the distal fold-over portion.

In a preferred embodiment, a mandrel is positioned within the sleeve of plastic material at a distal end of the stent device. The mandrel has a tapering profile that continues the tapering profile of the stent bed. The sleeve of plastic material is cold-drawn onto the mandrel, which provides a cold-drawn portion overlaying the stent device and a cold-drawn extension portion overlaying the mandrel. The extension portion is folded back over the stent device portion to provide a first, inner layer of the outer sheath and a second, outer layer of the outer sheath. When folded back, the second layer defines a reversely directed tapering profile, which increases a gap between the first layer and the second layer, which reduces the chances of sticking of the outer sheath during retraction of the outer sheath from the stent device.

The method can be further defined so as to provide the features of the stent device delivery system according to the above first, second, and third aspects of the invention and to provide features of the hereinbelow described further aspects of the present invention.

In a fifth aspect of the present invention, there is provided a stent device delivery system comprising a stent device and an outer sheath overlaying the stent device in a radially compact, delivery configuration of the stent device. The outer sheath is retractable to allow the stent device to radially expand to a deployed configuration. The stent device delivery system comprises a pull member for pulling proximally on to retract the outer sheath. A portion of the outer sheath is heat shrunk radially onto a relatively heat shrink resistant support member in order to capture a distal portion of the pull member radially between the outer sheath and the heat shrink resistant support member.

This aspect of the present invention offers a strong connection of the pull member to the outer sheath by making use of heat shrink material, which after heat shrinking, provides a compressive force on the pull member between the heat shrunk material and the support member. Further, without the features of the present aspect of the invention, the portion of the outer sheath that connects to the pull member is potentially subject to failure. In the present aspect of the invention, this portion is strengthened by heat-shrinking, which enhances the material properties of the heat shrink sheath. The support member is resistant to heat-shrinking, i.e. does not substantially change its properties at the relevant heat shrink temperature, compared to the portion of the outer sheath that has been heat shrunk. In use, the pull member is subjected to a proximal pulling force, which moves the pulling member, the outer sheath and the support member proximally with respect to the stent device to retract the outer sheath.

Preferably, the captured portion of the pull member extends an axial distance of at least about 1 inch (3 cm), at least about 2 inches (5 cm), or at least about 3 inches (8 cm). Preferably, the captured portion of the pull member defines a flattened profile with respect to the radial direction. These features both contribute to providing a strong attachment between the pull member and the outer sheath.

The portion of the outer sheath is heat shrunk onto the heat shrink resistant support member at an axial portion of the outer sheath that is proximal of the stent device. Exposing the stent device to heat, such as the heat required to heat shrink the outer sheath, is to be avoided especially in cases where the stent is manufactured from shape-memory alloys such as Nitinol. Similarly, exposing cold-drawn polymers, such as may be used to encapsulate the stent device, the heat will tend to negate the beneficial physical properties achieved by the cold-drawing process. By positioning the heat shrunk attachment of the pull member proximally of the stent device, a distinction can be made between a so-called "hot side" of the stent device delivery system that is proximal of the stent device and a so-called "cold side" of the stent device delivery system that consists of the remaining distal portion thereof.

The heat shrunk portion of the outer sheath provides a transition portion connecting the heat shrunk portion to a distal portion of the outer sheath overlaying the stent device. The transition portion tapers inwardly from the distal portion to the heat shrunk portion. Accordingly, a low profile heat shrunk portion, in which portion the pull member is attached to the outer sheath, is provided, which will allow it to be received in a sufficiently low profile delivery shaft extending back to a handle, control portion or access portion of the stent device delivery system. A transition section and a low profile portion proximal of it has, in prior art designs, provided a relatively lower strength area of the outer sheath, which has in turn led to deployment failure. The present invention provides heat shrunk material in this area to inhibit such possible failures.

In a preferred embodiment, the fifth aspect of the present invention is combined with the first aspect of the present invention, resulting in a pull member that is strongly attached to the outer sheath in a manner that is relatively simple to manufacture and forming a low profile stent device delivery system. More specifically, the outer sheath comprises a first layer and a reinforcement layer that are laminated together, preferably by a glue layer. The captured portion of the pull member is positioned radially between the first layer and the reinforcement layer, preferably embedded in and retained by the glue layer. The first layer and the reinforcement layer are heat shrunk onto the heat shrink resistant support member to capture the pull member radially between the outer of the two layers and the support member. Compression of the glue layer and pull member by the heat shrunk first layer and reinforcement layer enables an advantageously reduced profile to be obtained and, by reducing the thickness of any glue layer, enhances the bond strength between these elements.

The fifth aspect of the present invention can be applied to a rolling stent device delivery system. The outer sheath comprises an inner layer, an outer layer and a fold-over portion connecting the inner layer and the outer layer. The fold-over portion is axially movable relative to the stent device by moving the inner layer relative to the outer layer, thereby allowing the outer sheath to be retracted from the stent device. The outer layer is heat shrunk onto the heat shrink resistant support member to capture the pull member. Preferably, the outer layer includes the above-mentioned first layer and reinforcement layer laminated together, preferably by a glue layer. The first layer and the reinforcement layer are heat shrunk onto the heat shrink resistant support tube to capture the pull member. As stated above, the heat shrunk portion of the outer sheath and the captured portion of the pull member are positioned proximal of the stent device.

Preferably, the pull member is a pull wire, which is further preferably flattened at the captured portion.

In the rolling stent device delivery system, the inner layer is fixed relative to an inner catheter at a position proximal of the stent device. The outer layer is, in use, moved proximally relative to the inner layer to cause the fold-over portion to progressively approach the fixed proximal end of the inner layer during retraction of the outer sheath. In a preferred embodiment, a proximal end of the inner layer is heat shrunk radially onto the inner catheter to fix it thereto. This makes use of the previously-described concept of defining a "hot side" of the stent device delivery system where materials can be heat-shrunk, distinct from a "cold side". Heat shrinking offers a convenient, in terms of manufacturing, method of fixing the pull member to the outer sheath and the proximal end of the inner layer to the inner catheter.

Preferably, the proximal end of the inner layer of the outer sheath, which is fixed relative to the inner catheter, peels away under a pulling force as the fold-over portion, which defines the rolling edge, meets it and is pulled further proximally during retraction of the outer sheath. Heat shrink attachment of the inner layer to the inner catheter, relying on radial compression rather than adhesion to fix the inner layer to the inner catheter, is able to provide an appropriate peel force, low enough to allow the inner layer to come away from the inner catheter during retraction of the outer sheath, yet strong enough to otherwise, in use, stay fixed relative to the inner catheter.

The stent device is held fixed relative to the inner catheter by a holding mechanism presented by the inner catheter. Preferably, the holding mechanism is, at least in part, a stent bed according to the third aspect of the present invention described above.

A suitable material for the heat resistant support member is polyimide. A suitable heat shrinkable material for the outer sheath is polyethylene terephthalate (PET).

The generally described features of the fifth aspect of the present invention are combinable with any one or more of the features of the first to fourth aspects of the present invention in accordance with the corresponding combination of features given in the first, second and third embodiments of the present invention described in detail in the following.

In a sixth aspect of the present invention, there is provided a method of making a stent device delivery system. The method comprises providing a stent device and an outer sheath overlaying the stent device in a radially compact delivery configuration of the stent device, wherein the outer sheath is retractable to allow the stent device to radially expand to a deployed configuration. The method further comprises a step of providing a pull member for attachment to the outer sheath to be subjected to a proximal pulling force to effect retraction of the outer sheath. The method yet further comprises a step of positioning a relatively heat shrink resistant support tube within the outer sheath, at a position axially proximal of the stent device. The method even yet further comprises a step of radially heat shrinking a portion of the outer sheath onto the support tube to capture the pull member radially between the outer sheath and the support tube.

In a preferred embodiment, the method further comprises forming the outer sheath to include a first layer and a reinforcement layer. The method comprises a step of laminating the reinforcement layer to the first layer to retain the pull member radially between the first layer and the reinforcement layer. Preferably, the first layer is glued to the reinforcement layer and the pull member is embedded in a glue layer gluing the first layer and the reinforcement layer together. The first layer and the reinforcement layer are heat shrunk onto the support tube as described above to capture the pull member radially between the outer sheath layer and the support tube.

Preferably, the method further comprises loading a stent device into a sleeve of material for forming the outer sheath. The sleeve of plastic material is cold-drawn to reduce the diameter of the sleeve and to reduce the diameter of the stent device to put the stent device in the radially compact, delivery configuration. The stent device is thus provided with an outer sheath overlaying the stent device in a radially compact, delivery configuration. The outer sheath is retractable to allow the stent device to expand to a radially expanded, deployed configuration. In a preferred embodiment, the sleeve of plastic material is cold-drawn by application of endwise tension onto a mandrel positioned at a distal end of the stent device to provide a first portion of cold-drawn sleeve overlaying the stent device and an extension portion of cold-drawn sleeve overlaying the mandrel. The extension portion is folded back onto itself to overlay the stent device so that the outer sheath comprises an inner layer comprising the first portion, an outer layer formed by the extension portion and a fold-over portion connecting the inner layer and the outer layer, thereby providing a rolling stent device delivery system.

A proximal end of the sleeve of plastic material is fixed to the inner catheter by heat shrinking the inner layer thereto at a position axially proximally of the stent device, that is to say at a position opposite to a distal end of the stent device where the fold-over portion will be located.

After folding the sleeve of material onto itself to form the inner layer and the outer layer as described above, the reinforcement layer, being a further sleeve of plastic material, is placed coaxially over the interim outer layer of the outer sheath and laminated, preferably glued, thereto to form an outer layer having a first layer and a reinforcement layer that are laminated together, preferably by a glue layer radially positioned therebetween. The outer layer comprising the first layer, the preferred glue layer and the reinforcement layer is heat shrunk onto the support tube at a position axially proximal of the stent device with the pull member embedded between the first layer and the reinforcement layer, preferably embedded in the glue layer, thereby capturing the pull member radially between the outer sheath and the support tube as described above.

The stent bed and optionally the mandrel may have a tapered profile and the stent device delivery system may be produced in accordance with the description given above for the fourth aspect of the present invention. Further, the method may be configured to produce features of the systems of any one or a combination of the first, second, third and fifth aspects of the present invention.

There are generally applicable features of the present invention, in any of its aspects, that have yet to be described.

The stent device delivery system preferably comprises a tip at a distal end thereof. The tip may taper inwardly in a distal direction in order to ease insertion into narrow passages. The tip preferably comprises an annular notch for stationing the fold-over portion.

Preferably, the outermost layer of the outer sheath is hydrophilic. Preferably, it is the outer surface of the reinforcement layer that is hydrophilic. The purpose of this is to ease passage of the stent device delivery system during delivery to provide a lubricated distal surface of the system for ease of passage during delivery.

The provision of an outermost layer of an outer sheath of a stent delivery system is an independently applicable modification to the prior art. Thus, it is disclosed to have a stent device delivery system comprising a stent device and an outer sheath overlaying the stent device in a radially reduced, delivery configuration. The outer sheath is retractable to uncover the stent device to allow the stent device to expand radially to a deployed configuration. An outermost surface of the outer sheath is hydrophilic along at least a distal axial portion thereof overlaying the stent device.

Preferably, the stent device is a self-expanding stent device. Self-expanding stent devices are biased from the delivery configuration to the radially expanded, deployed configuration at body temperature. Suitable self-expanding stent devices for application in the present invention are well-known to the skilled person, and may be manufactured from shape-memory alloys, such as Nitinol.

In the case of a self-expanding stent device, the radially reduced, delivery configuration is a radially compressed, delivery configuration. The outer sheath restrains the stent device in the radially compressed, delivery configuration. Retraction of the outer sheath releases the stent device to self-expand to the radially expanded, deployed configuration.

The present invention will be further understood from the detailed description of the first, second and third stent device delivery system given below. The detailed description will also be useful for the skilled person in providing guidance, although without limitation as to the combinability of the various features of the various aspects of the present invention given above.

The laminate of the first layer and the reinforcement layer are thinner than state of the art outer sheaths. The first layer and the reinforcement layer are both between 30 and 40 μm thick in the radial direction. Preferably, the resulting laminate is less than 100 μm thick, preferably between 70 and 90 μm. Despite this reduced thickness, the laminate maintains the required strength characteristics.

DETAILED DESCRIPTION

Figures 1, 2:
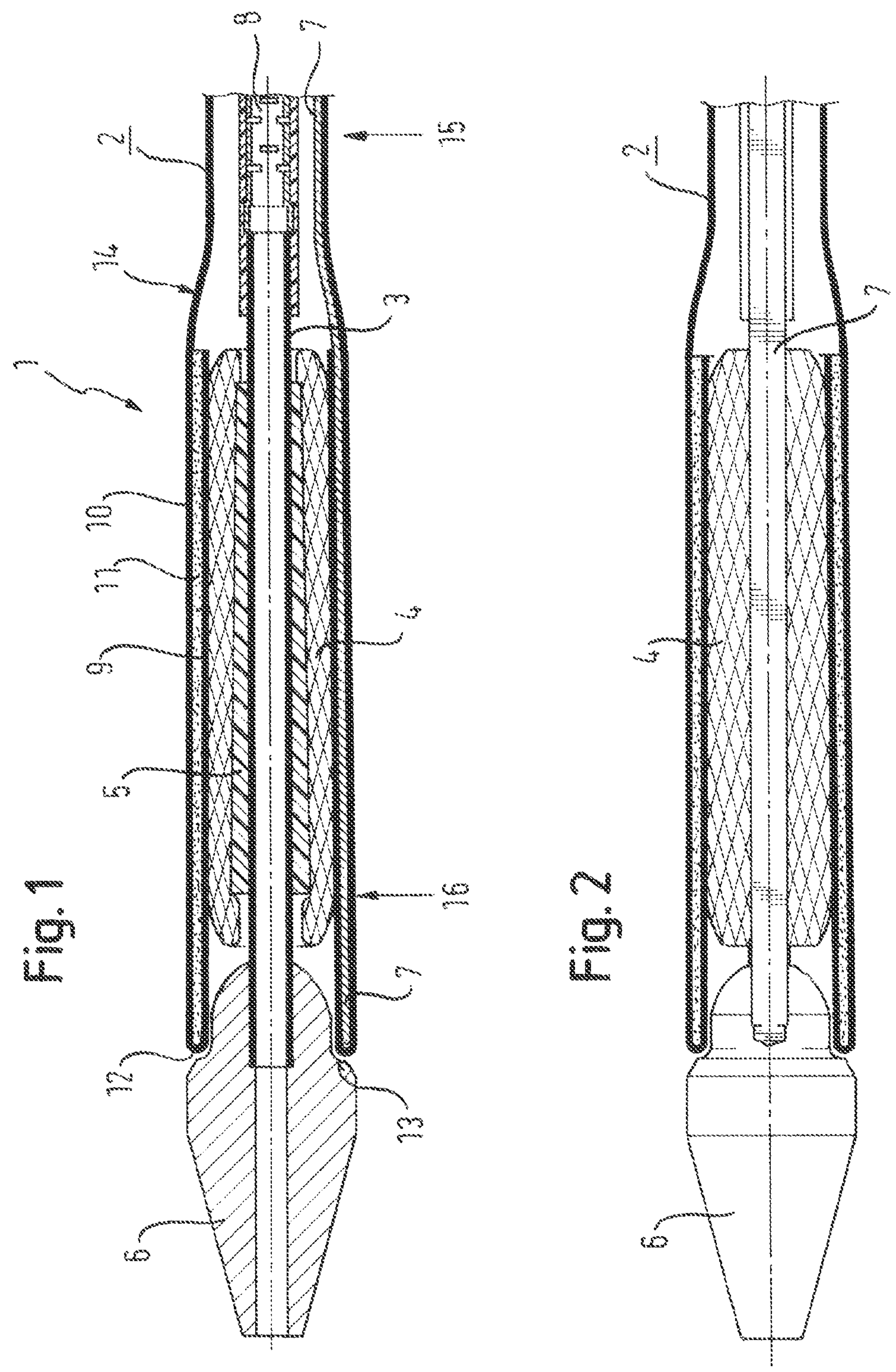
FIG. 1 shows a stent device delivery system of the pullback type, where the axial portion of the outer sheath overlaying the stent device is formed from a lamination of first and second layers of polymeric material. A pull wire is embedded radially between the first and second layers and extends to the distal end of the outer sheath.
FIG. 2 shows a view of the stent device delivery system of FIG. 1 whereby the stent device delivery system is rotated by 90° if one takes the proximal to distal direction as pointing to the clock face. This particular cross-section shown allows the pull member to be clearly viewed.

A first stent device delivery system 1 is shown in FIGS. 1 and 2. The stent device delivery system 1 comprises an inner catheter 3 having a stent bed 5 mounted on the inner catheter 3. A stent device 4 is clamped onto the stent bed 5 so that the inner surface of the stent device 4 engages with the outer surface of the stent bed 5. An outer sheath 2 extends over the stent device 4 to constrain the stent device 4 in the radially reduced, delivery configuration shown, where the inner surface of the stent device 4 engages the outer surface of the stent bed 5. The outer sheath 2 is retractable relative to the inner catheter 3 and the stent device 4, and thus to position an end of the outer sheath 2, which is a distal end of the outer sheath 2, proximally of the stent device 4 to a retracted position. The retracted position of the outer sheath 2 frees the stent device to expand radially from the delivery configuration shown to a deployment configuration for supporting a diseased vascular lumen. The stent device shown is preferably a self-expanding stent device and moves to the deployed configuration, once the outer sheath 2 is retracted, by material memory. As the outer sheath 2 is retracted, the stent bed 5 serves to hold the stent device 4 axially stationary relative to the inner catheter 3. The stent bed 5 is axially distributed along the inner surface of the stent device 4 from about a proximal end to about a distal end of the stent device 4 to ensure a sufficient holding force to resist the outer sheath 2 causing axial displacement of the stent device 4 relative to the inner catheter 3. Other means for holding the stent device 4 relative to the inner catheter, such as a stop proximal of the stent device, are known in the art and would be suitable for this purpose.

The outer sheath 2 is made from a polymeric material comprising a first, outer layer 10 and a second, inner layer 9 acting as a reinforcement layer 9. A glue layer 11 is radially interposed between the first layer 10 and the reinforcement layer 9. The first layer 10 and the reinforcement layer 9 are laminated to one another by the glue layer 11 sandwiched radially therebetween. The glue layer 11 is distributed circumferentially around the outer sheath 2. The laminated first and reinforcement layers 9, 10 extend from about a proximal end of the stent device to about a distal end of the stent device. In fact, in the system 1 shown, the first and second layers 9, 10 extend beyond a distal end of the stent device 4. Connecting the first and second layers 9, 10 is a fold-over portion 12 at the distal end of the outer sheath 2. An inner surface of the reinforcement layer 9 is in contact with an outer surface of the stent device 4.

A pull member 7 for retracting the outer sheath 2 is positioned radially between the laminated first and reinforcement layers 9, 10 of the pull member 7 at a distal end portion of the pull member 7. The glue layer 11, which adheres the first and reinforcement layers 9, 10 together is spread along the distal portion of the pull member 7 and contacts the pull member 7 to adhere the first and reinforcement layers 9, 10 of the outer sheath 2 to the distal portion of the pull member 7 as well as to each other. The pull member 7 is a wire in the shown embodiment that has been flattened along the distal portion as compared to a proximal portion of the pull member 7, which is cylindrical. The distal portion of the pull member 7 extends along the stent device 4 from a proximal end to a distal end of the stent device 4 and in the shown system 1, to a distal end of the outer sheath 2.

FIGS. 1 and 2 also show a tip member 6 attached to the inner catheter 3. The tip member 3 has a recess 13, which receives a distal end of the outer sheath 2. The tip member 6 has a middle, in the axial direction, section that is of the same diameter as the outer sheath 2 and tapers radially inwardly towards the distal end of the tip member 6. In FIG. 1, the inner catheter 3 can be seen as a simple tube in the axial portion where the stent bed 5 and the stent device 4 is located. At a position proximal of the stent device 4, the simple tube of the inner catheter 3 is connected to a guide portion 8 of the inner catheter 3 that comprises an inner tube and a tubular sleeve overlaying the inner tube, where the inner tube has formed through the wall thickness a plurality of axially distributed slits formed so that the extent of each slit in the circumferential direction exceeds half of the circumference of the tube to allow the guide portion of the inner catheter to be flexed. The configuration of the guide portion of the inner catheter is the subject of International Patent Application No. PCT/EP2010/060559, which is incorporated by reference in its entirety into this application. The guide portion 8 of the inner catheter 3 will not be described in further detail in the present application. A suitable material for the simple tube portion of the inner catheter 3 is polyamide.

Lamination of the first and reinforcement layers 9, 10 by the glue layer 11 allows the outer sheath 2 to be made from polymeric first and reinforcement layers 9, 10. Usually, and particularly for long stent devices, this would mean that the outer sheath 2 would be stressed to failure or necking as the outer sheath 2 moves over the stent device 4 because of the drag force between the inner surface of the outer sheath 2 and the outer surface of the stent device 4. Necking of the outer sheath 2 could also cause failure of the outer sheath 2 during retraction because it would too tightly grip the stent device 4, which would cause a required retraction force greater than the breaking strength of the outer sheath 2. The combination of first and reinforcement layers 9, 10 and a means for laminating the first and reinforcement layers 9, 10 together has been found to be surprisingly resistive to necking of the outer sheath 2 during retraction of the outer sheath 2 as well as to provide strength benefits beyond the mere combination of the layers 9, 10.

The outer sheath 2 is an integral structure in that the first layer 9 and the second layer 10 are made from the same tube of material, which is folded back upon itself and glued together to form the reinforcement layer 9, the first layer 10 and the connecting portion 12 between the first. The outer sheath 2 includes a transition portion 14 connecting a distal axial portion 16 of the outer sheath 2, overlaying the stent device 4, and a proximal portion 15. The transition portion 14 tapers inwardly from the distal portion 16 to the proximal portion 15, as the proximal portion 15 has a radially reduced configuration as compared to the distal portion 16. This allows the radial bulk of the stent device 4 to be accommodated at the distal portion and allows a reduced profile guide portion at the proximal portion 15. The transition portion 14 is particularly susceptible to failure during retraction of the outer sheath 2. Accordingly, in an alternative to that shown in FIGS. 1 and 2, the reinforcement provided by the laminated first and reinforcement layers 9, 10 can extend proximally beyond that shown so that the laminated first and reinforcement layers 9, 10 form the outer sheath in the distal portion 16 as well as the tapering portion 14 and/or at least some of the proximal portion 15.

Figure 6:
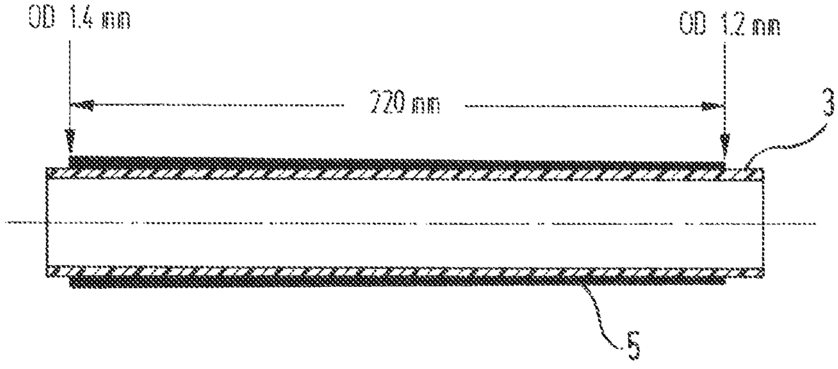
FIG. 6 shows a tapering stent bed design. The tapering stent bed is also shown in the system of FIGS. 1 to 4. The tapering stent bed is continuous from a radially larger distal end to a radially smaller proximal end.

The stent bed 6 shown in FIGS. 1 and 2 has a tapering profile from a larger outside diameter distal end to a smaller outside diameter proximal end. Receiving the stent device 4 on such a stent bed 5 is advantageous for reasons discussed further below. Examples for the tapering profile of the stent bed can be seen in FIGS. 6 and 7. In FIG. 6, the stent bed is formed by a continuous layer applied to the inner catheter 3. The stent bed 5 has a thicker profile at one end, the distal end, than at the other end, the proximal end, of the stent bed 5. In the embodiment shown, the stent bed 5 tapers radially inwardly in a linear fashion from the distal end to the proximal end. The layer could, however, reduce in thickness in the radial direction in a stepwise fashion or in some other non-linear curved arrangement, such as in an exponential fashion. In FIG. 6, the outside diameter of the stent bed 5 is 1.4 mm at the distal end and 1.2 mm at the proximal end and has an axial length of 220 mm. A gradient for the tapering profile can be worked out by taking the maximum change in thickness over the length of the stent bed 5 and dividing this value by the length of the stent beds, which gives (1.4−1.2)/220=0.00091, or 0.091%.

Figure 7:
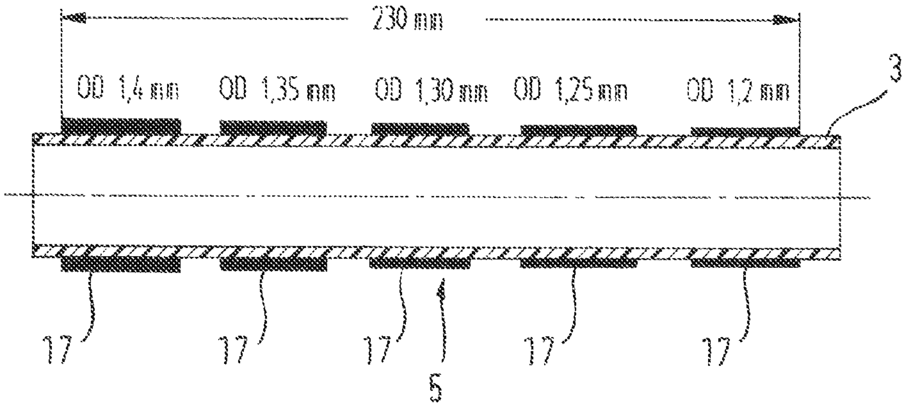
FIG. 7 shows an alternative design for a tapering stent bed, which is made up of axially separated band members, where the band members reduce in thickness from a distal end of the stent bed so as to define a tapering stent bed.

In FIG. 7 an alternative arrangement for the stent bed 5 is shown. The stent bed 5 is formed by a plurality of axially separated band members 17. The band members 17 thus define axially distributed gaps between each pair of band members 17 in the stent bed 5. In the embodiment of FIG. 6, there are five band members 17, but the use of more band members or indeed one or two fewer band members is envisaged as being functional. Each band member 17 has a constant outer diameter while the set of band members 17 reduce progressively in thickness from the distal end to the proximal end. Each band member 17 may have a constant thickness as shown so as to define a constant outside diameter for the stent bed 5 along the axial portion where the band member 17 is located. Alternatively, each band member 17 could itself define a tapering profile. This tapering profile could follow a linear path from the distal end of the stent bed 5 to the proximal end. In another variation, each band member 17 could itself define a tapering profile following a stepwise or non-linear path. In the example of FIG. 7, the most distal band member 17 defines an outside diameter for the stent beds of 1.4 mm, the second most distal band member 17 defines an outside diameter for the stent beds of 1.35 mm, the middle band member 17 defines an outside diameter for the stent beds of 1.30 mm, the second most proximal band member 17 defines an outside diameter of 1.25 mm and the most proximal band member defines an outside diameter of 1.20 mm. The stent bed 5 extends over an axial length of 230 mm. Accordingly, the gradient of the tapering profile of the stent bed 5 is (1.4−1.2)/230=0.00087, or 0.087%. Other lengths of stent beds are envisaged from 100 mm to 350 mm, for example. A range of maximum change in the outside diameter of the stent bed 5 could be from 0.1 mm to 0.4 mm, for example. The earlier given ranges for the gradient of the tapering profile of the stent bed 5 are preferred, and particularly gradients in the range 0.01% to 0.1%, more preferably 0.05% to 0.1%, are desirable.

The stent bed 5 of FIG. 6 could be made by spraying rubber or silicone glue onto the inner catheter 3. A Dymax medical adhesive layer for the stent bed 5 is also envisaged. In the example of FIG. 7, the stent bed 5 may be formed by polyether block amide (PEBAX) or a Dymax adhesive. The band members 17 are preferably formed on the inner catheter 3, rather than formed separately and slid over the inner catheter 3 into position. These materials are chosen because they offer a tacky and deformable stent bed 5 for receiving the stent device 4. The tacky stent bed 5 provides a slight radial force against expansion 4. The stent bed 5 will naturally provide an axial holding force for the stent device 4 relative to the inner catheter 3 by friction between the stent device 4 and the stent bed 5. Further, the deformability of the stent bed 5 allows the stent device 4 to be partially embedded into the outer surface of the stent bed 5, which will provide a form fit between the stent device 4 and the stent bed 5, which further ensures a sufficient hold of the stent device 4 relative to the inner catheter 3. The use of a stent bed 5 that is distributed along an inner surface of a stent device 4 from a proximal end to a distal end of the stent device 4 and having tackiness and deformability properties is discussed in WO 2010/031755, which is incorporated by reference in its entirety into this application. The stent bed 5 may be non-tapered in accordance with stent beds known in the art such as in WO 00/71058, which is incorporated by reference in its entirety into this application. In another alternative, a push element proximal of the stent device 4 may be used to hold the stent device 4 relative to the inner catheter 3. Such a proximal push element is disclosed in FIGS. 1 and 2 of WO 00/71058, for example.

The tapered profile design for the stent bed 5 is advantageous for the following reasons. In a pullback outer sheath design as shown in FIGS. 1 and 2, the retraction force or the drag between the outer sheath 2 and the stent device 4 is at its greatest when relative movement between the stent device 4 and the outer sheath 2 begins. The larger diameter portion of the stent bed 5 is more strongly compressed by the stent device 4 than the smaller diameter proximal portion and thus provides a greater holding force towards the distal end of the stent device 4. Also, the larger diameter portion pushes the stent device 4 more strongly into the outer sheath 2, causing a greater drag force between the stent device 4 and the outer sheath 2 at the distal end. The tapering profile of the stent bed 5 is believed to provide sufficient holding force at the distal end, where it is needed most, while the reducing diameter lessens the overall drag force between the stent device 4 and the outer sheath 2 as a whole, as compared to if the stent bed 5 had a constant diameter equal to the outside diameter of the stent bed 5 at the distal end. Accordingly, the force required to retract the outer sheath 2 is reduced overall, while ensuring sufficient holding of the stent device 4 relative to the inner catheter 3 for a correct placement of the stent device 4 at the target site. The reduced deployment force allows thinner polymeric materials to be used for the outer sheath 2 to contribute to a reduced profile design of the stent device delivery system 1.

Returning to the stent device delivery system 1 shown in FIGS. 1 and 2, deployment of the stent device 4 will be described. A guidewire is first fed through the tortuous passageways of the vasculature of a patient so as to arrive at the site of the diseased vascular lumen that requires support by a stent device 4. The stent device delivery system 1 of FIGS. 1 and 2 is then fed along the guidewire by the guidewire being received in a lumen of the inner catheter 3. The tapering profile of the nozzle 6 aids delivery because it provides a smooth distal surface for easing passage of the stent device delivery system 1 through the vasculature of the patient. A correct position of the stent device delivery system 1 at the target site is determined by radioimaging, making use of a radiopaque material positioned at the distal and proximal ends of the stent device 4. In order to deploy the stent device 4, the surgeon operates a hand-held portion of the system 1 to cause the pull member 7 to be pulled back relative to the stent device 4.

As the pull member 7 is caused to move proximally, the first and reinforcement layers 9, 10 of the outer sheath 2 move as a single laminar structure relative to the stent device 4. Axial movement of the outer sheath 2 relative to the stent device 4 causes the inner surface of the outer sheath 2 to drag over the stent device 4. This drag force tends to force the stent device 4 in the proximal direction relative to the inner catheter 3. The engagement between the outer surface of the stent bed 5 and the inner surface of the stent device 4 resists any proximal movement of the stent device 4 to hold the stent device 4 fixed relative to the inner catheter 3. As the distal end or connecting portion 12 of the outer sheath 2 moves over the stent device 4, the stent device 4 is released from the outer sheath 2 progressively in a proximal direction.

The stent device 4 when released expands radially from its delivery configuration shown in FIGS. 1 and 2 to a deployed configuration for supporting the diseased vascular lumen. The stent device 4 is fully deployed once the distal end of the outer sheath 2 is positioned entirely proximally of a proximal end of the stent device 4, which is when the outer sheath is considered retracted from the stent device 4. Extending the pull member 7 so as to overlay the stent device 4 and be attached to the outer sheath 2 at a location distal of the transition section 14 of the outer sheath 2 reduces the chance of failure of the outer sheath 2 because the pull member 7 greatly contributes to the axial strength of the outer sheath 2. The further the pull member extends distally relative to the outer sheath 2, the greater axial distance the outer sheath is reinforced by the pull member 7. Hence, in the preferred configuration shown in FIGS. 1 and 2, the pull member 7 extends to the distal end of the outer sheath 2. The lamination of the first and reinforcement layers 9, 10, particularly by use of a glue layer 11 as shown, provides necking resistance for the outer sheath 2 and also axial strength to avoid sticking of the outer sheath 2 on the stent device 4 and potential failure of the outer sheath 2 during retraction.

In an alternative to that shown in FIGS. 1 and 2, the pull member 7 may be attached at a position proximal of the stent device 4 and proximal of the transition section 14 of the outer sheath 2. In this arrangement, the reinforcement layer 9 would be extended also proximal of the stent device 4 so that the pull member 7 is still attached by lamination radially between the first layer 10 and the reinforcement layer 9. The outer sheath would not then be reinforced by the pull member 7 along an axial portion where the stent device 4 is located, which would mean that the distal portion 16 of the outer sheath 2 must be sufficiently strong to manage the axial forces during retraction without necking, sticking or breaking. The reinforcement to the first polymeric layer 10 of the outer sheath 2 provided by the lamination with the reinforcement layer 9 and preferably also the glue layer 11 thus takes on particular importance in this alternative arrangement. This alternative could be further modified by heat shrinking the first layer 10 and the reinforcement layer 9 onto a heat shrink resistant support tube located axially within the proximal portion 15 of the outer sheath. The pull member 7 would still be located radially between the first layer 10 and the reinforcement layer 9. Heat shrink attachment, as well as attachment by lamination, of the pull member 7 ensures secure attachment of the pull member 7 to the outer sheath 2. Such heat shrink attachment is discussed further below with respect to FIGS. 4 and 5.

Figure 3:
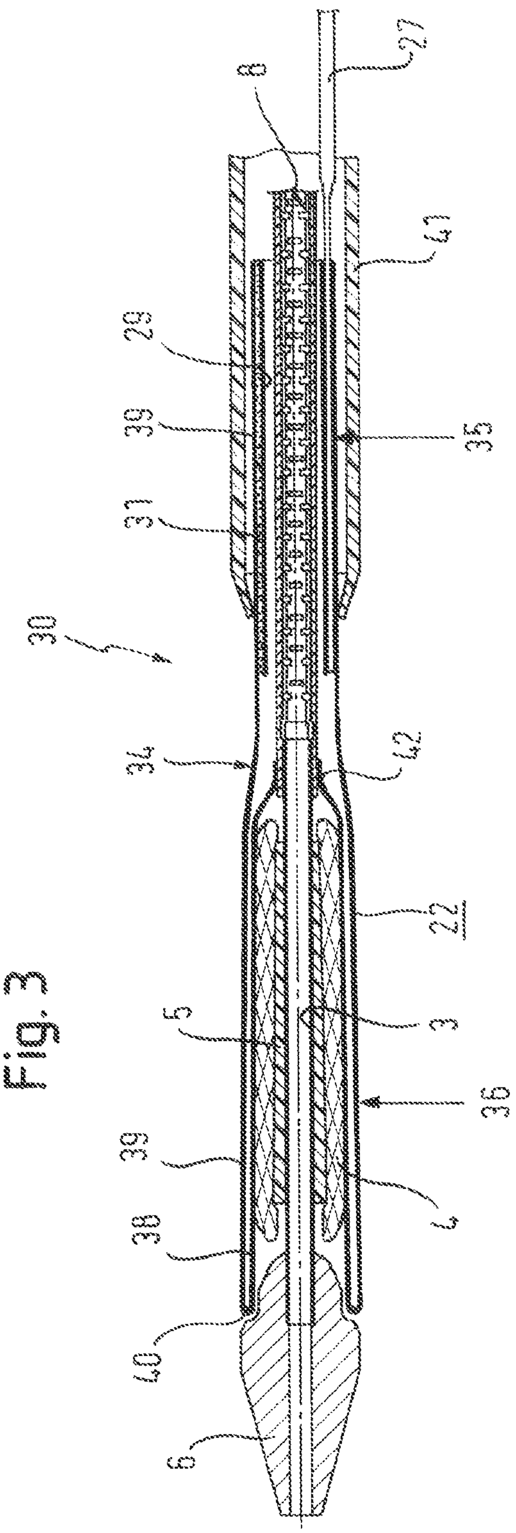
FIG. 3 shows a stent device delivery system of the type having a rolling outer sheath. Further, the pull member is attached to an outer layer of the outer sheath at a position proximal of the stent device by laminating a first layer of polymeric material to the outer layer and sandwiching the pull member radially therebetween.

FIG. 3 shows another exemplary stent device delivery system. Where like elements are referred to, the same reference numeral has been used as in FIGS. 1 and 2.

The stent device delivery system 30 of FIG. 3 has an outer sheath 22 of the rolling kind. As before, a stent bed 5 having a profile tapering radially inwardly from a distal end to a proximal end is mounted to an inner catheter 3. A stent device 4 overlays the stent bed 5 and the inner surface of the stent device 4 engages with the outer surface of the stent bed 5 to provide an interaction holding the stent device 4 relative to the inner catheter 3. In a distal portion 36 of the outer sheath 22 overlaying the stent device 4, the outer sheath 22 is formed into an outer layer 39 that is folded over an inner layer 38 and connected by a fold-over portion 40. The outer layer 39 is axially moveable relative to the inner layer 38 in a proximal direction, which causes the fold-over portion 40 to roll proximally, thereby effecting retraction of the outer sheath 22. The inner layer 38 is attached to the inner catheter 3 at a location proximal of the stent device 4.

The outer layer 39 extends proximally beyond the inner layer 38 to provide a proximal portion 35 of the outer sheath 22 that is attached to a pull member 27. The pull member 27 is attached to the outer sheath 22 by lamination with a reinforcement layer 29. The pull member 27 is captured radially between the laminated outer layer 39 and the reinforcement layer 29. The reinforcement layer 29 is, in system 30 shown in FIG. 3, located radially inwardly of the outer layer 35 of the outer sheath 22. The reinforcement layer 29 could, however, be disposed outwardly of the outer layer 34 of the outer sheath 22. The outer layer 39 and the reinforcement layer 29 are laminated together by a glue layer 31 distributed circumferentially around and axially along the reinforcement layer 29. The pull member 27 is embedded in the glue layer 31, which provides an adhesive connection to the reinforcement layer 29 and the outer layer 39 as well as a connection by the capturing effect of the laminated layers 29, 39. The glue layer is preferably a medical adhesive sold under the trade name Dymax. It may be UV curable for ease of manufacturing. This is also a suitable material for the glue layer 11 of the system 1 of FIGS. 1 and 2.

The stent bed 5 shown in FIG. 3 is again of the tapering profile form. The tapered profile of the stent bed 5 has been discussed above with respect to FIGS. 1, 2, 6 and 7. A non-tapered stent bed alternative was also discussed as well as a means for holding the stent device 4 relative to the inner catheter that is positioned proximal of the stent device 4. Such alternative stent device holding means is also applicable to the system 30 shown in FIG. 3.

FIG. 3 also shows a guide sheath 41 of the stent device delivery system 30 from which the inner catheter 3, the stent device 4 and the outer sheath 22 extend to allow the stent device 4 to expand to the deployment position when the outer sheath 22 is retracted. The outer guide sheath 41 can be made of conventional material that is suitably flexible to navigate the vasculature of the patient yet suitably strong under endwise compression to allow it to be delivered to the target site by an operative at a proximal end outside of the patient. Also shown in FIG. 3 is the inner catheter 3 being made up of a conventional tube at a distal portion and a proximal guide portion 8 made of a slitted tubular material and an outer tubular sleeve as described above with respect to FIGS. 1 and 2.

Deployment of the stent device delivery system 30 of FIG. 3 is effected by subjecting the pull member 27 to a proximal pulling force. The pull member 27 is securely attached to the outer layer 39 of the outer sheath 36 by a combination of being captured between the laminated layers 29 and 39 and also by adhesive attachment with these layers by the glue layer 31. Thus, the outer layer 39 is moved proximally as the pull member 27 is moved proximally and the outer layer 39 moves relative to the inner layer 38 by action of the fold-over portion 40 rolling proximally. As the fold-over portion 40 moves proximally and begins to uncover the stent device 4, the stent device 4 expands from the delivery configuration shown in FIG. 3 to a deployed configuration. Once the fold-over portion 40 is proximal of the stent device 4, the stent device 4 is able to fully deploy along the full axial length of the stent device 4. The fold-over portion 40 of the outer sheath 22 will continue to roll proximally as the pull member 27 is moved proximally until it reaches a connection portion 42 of the inner layer 38 of the outer sheath 22 to the inner catheter 3. In the embodiment shown in FIG. 3, the connection portion 42 is releasable under a slight additional pulling force on the outer layer 39 of the outer sheath 22 so that the outer sheath 22 can be retracted independently of the inner catheter, if desired.

The inner layer 38 of the outer sheath 22, in a portion overlaying the stent device 4, will be induced to share the tapering profile of the stent bed 5. Thus, a distal end of the inner layer 38 will have a larger outside diameter than a proximal end of the inner layer 38. As the distal end of the inner layer 38 folds over itself to form the rolling fold-over portion 40, at each instant the outer layer 39 has a larger diameter in the vicinity of the rolling edge than the inner layer 38. This provides a gap between the inner layer 38 and the outer layer 39 allowing the outer layer 39 to slide over the inner layer 39 with reduced opportunity sticking or catching between the two layers 38, 39. This feature thus both reduces deployment force of the rolling outer sheath 22 and improves reliability of successful retraction of the outer sheath 22. As will be described below, with reference to methods of manufacture of the stent device delivery systems disclosed herein, the inner layer 38 of the outer sheath 22 is preferably formed to have a tapering profile substantially the same as the stent bed 5 to ensure the formation of the gap described above. The inner layer 38 may be formed to have the tapered profile by cold-drawing the inner layer 38.

In an alternative stent device delivery system to that shown in FIG. 3, the reinforcement layer 29 could be extended further so that it covers not just the proximal portion 35 of the outer sheath 22, but also the transition section 34 where the outer sheath 22 tapers radially inwardly the distal portion 36 overlaying the stent device 4 the radially reduced proximal portion 35. The transition section 34 of the outer sheath 22 is at increased risk to failure and thus reinforcement of this portion, by the lamination of the reinforcement layer 29 thereto, may be particularly useful. The reinforcement layer 29 in this alternative configuration thus captures the pull member 25 in a proximal portion of the reinforcement layer 29 while the reinforcement 29 continues distally beyond the distal end of the pull member 27 to further act in a reinforcement capacity for the transition section 34 of the outer sheath 22. The reinforcement layer 29 may further extend distally beyond the transition section 34 to overlay the stent device 4 and be laminated to the distal portion 36 of the outer layer 39. This provides reinforcement to the outer layer 39 to avoid necking of the outer layer 39 which would otherwise cause the outer layer 39 to contact and compress the inner layer 38, thereby causing the rolling action of the outer sheath 28 to stick and potentially fail. An extended reinforcement layer 29 would provide the necessary resistance to such potential failure in the outer layer 39 of the outer sheath 22.

In another alternative to that shown in FIG. 3, a heat shrink resistant support tube could be placed radially within the outer layer 39 and the reinforcement layer 29. The outer layer 39 and the reinforcement layer 29 could be heat shrunk onto the support tube to further secure the attachment of the pull member 27. This means of attachment of the pull member 27 to the outer sheath 34 is described below with respect to the delivery system 60 shown in FIGS. 4 and 5.

In yet another alternative, the pull member 27 may be extended further distally to that shown in FIG. 3 so as to overlay the stent device 4. The reinforcement layer 2*a* would also be extended distally so that the pull member would still be captured radially between the laminated outer layer 39 and reinforcement layer 29. Having the pull member 27 extend substantially to a distal end of the outer sheath 34 or at least so as to overlay the stent device can be advantageous as discussed earlier with reference to FIGS. 1 and 2. In particular, the pull member 27 provides tension support to the outer sheath 34 throughout the length of sheath to which it is laminated.

Figure 4:
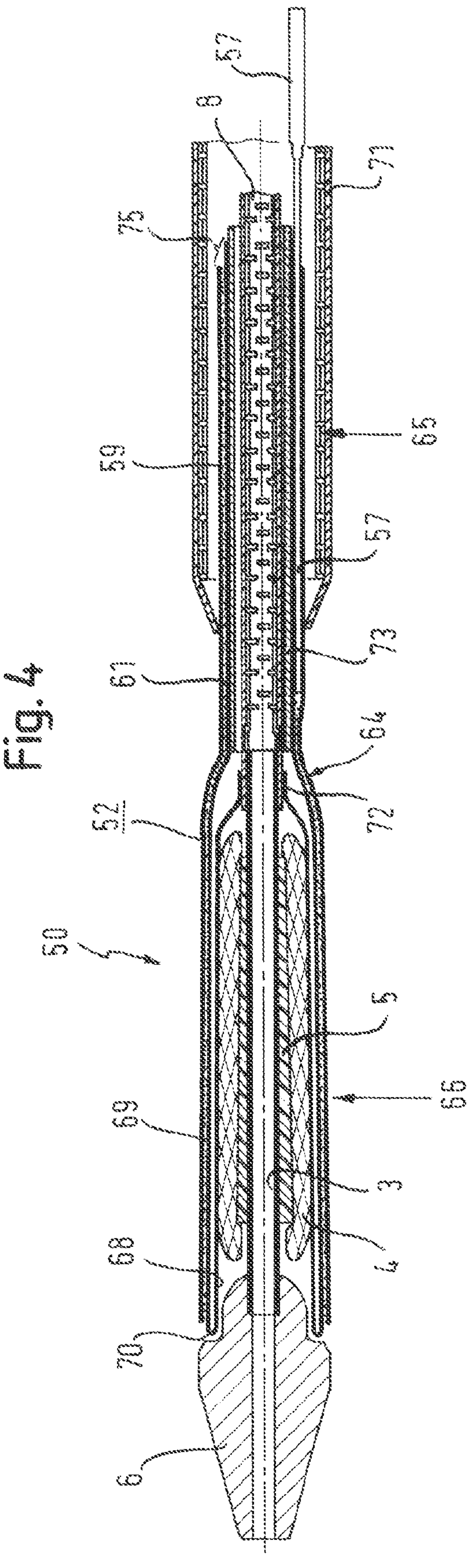
FIG. 4 shows another stent device delivery system of the rolling kind having an outer sheath that is retracted by rolling an outer layer over an inner layer. Further, a reinforcement layer is laminated to the outer layer, which reinforcement layer extends axially from a position proximal of the stent device to a position overlaying the stent device. The pull member is attached to the outer layer of the outer sheath by being sandwiched radially between the outer layer and the reinforcement layer in the lamination of these two layers. The stent device delivery system includes a heat shrink resistant support tube and the outer layer is heat shrunk onto the heat shrink support tube. The heat shrink support tube is positioned proximally of the stent device.
Figure 5:
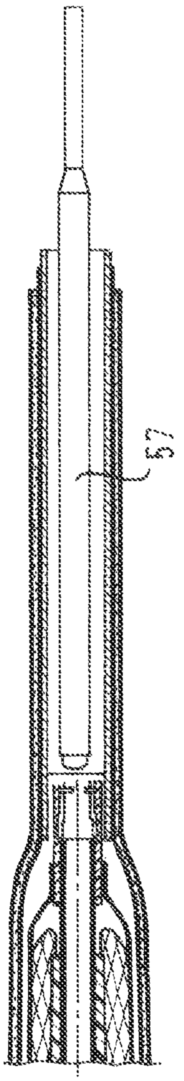
FIG. 5 shows a view of the stent device delivery system of FIG. 4 that has been rotated 90° clockwise and in a particular cross-section to better show the pull member.

The stent device delivery system 50 shown in FIGS. 4 and 5 is the presently most preferred delivery system. It combines the low retraction force of a rolling outer sheath 52 with full reinforcement by a reinforcement layer 59, more reliable retraction of the outer sheath 52 by the provision of a stent bed 5 having a tapering profile and secure attachment of the pull member 57 to the outer sheath 52 by lamination of the reinforcement layer 59 to an outer layer 69 of the outer sheath 52 and also by means of other advantageous features that have not yet been described.

In this system, the stent device 4 is radially constrained by the outer sheath 52 into engagement with the tapered stent bed 5. The outer sheath 52 comprises an inner layer 68 having an inner surface contacting an outer surface of the stent device 4 and an outer layer 69 that are connected at a distal end of the outer sheath 52 by a fold-over portion 70. The outer layer 69 is axially movable in the proximal direction relative to the inner layer 68, which causes the fold-over portion 70 to move proximally as well, thereby retracting the outer sheath 52. The inner layer 68 of the outer sheath 52 is connected to the inner catheter 3 at a connecting portion 72 located proximally of the stent device 4. The outer layer 69 of the outer sheath 52 extends further proximally from the connecting portion 72 to a distal portion of a pull member 57. The distal portion of the pull member 57 is sandwiched between the outer layer 69 and a reinforcement layer 59 that is laminated to the outer layer 69 to attach the pull member 57 to the outer sheath 52. In the system 50 shown in FIG. 4, the reinforcement layer 59, as opposed to the system 30 shown in FIG. 3, is positioned radially outside of the outer layer 69.

The reinforcement layer 59 and the outer layer 69 are laminated together to capture the distal portion of the pull member 57 and this is preferably done by spreading a glue layer 61 axially along the full length of the reinforcement layer 59 and circumferentially around the reinforcement layer 59. The distal portion of the pull member 57 is, therefore, embedded in the glue layer 61 and adhered to the reinforcement layer 59 and the outer layer 69. The reinforcement layer extends further along the stent device delivery system 50 than in the system 30 shown in FIG. 3. The reinforcement layer 59 in the system 50 shown in FIG. 5 extends substantially to a distal end or fold-over portion 70 of the outer sheath 52. The reinforcement layer 59, the glue layer 61 and the outer layer 69 can together be considered an outer layer of the outer sheath 52. The inner layer 68 and this combined outer layer then make up the outer sheath 52. Accordingly, we will refer to the layer 69 as the second layer and the combination of the second layer 69, the glue layer 61 and the reinforcement layer 59 as the outer layer 75 of the outer sheath 52 in the following.

Attachment of the distal portion of the pull member 57 to the outer sheath 52 is enhanced by heat shrinking the second layer 69 and the reinforcement layer 59 with the distal portion of the pull member 57 captured radially between these layers 59, 69. The reinforcement layer 59 and the second layer 69 are heat shrunk onto a heat shrink resistant support tube 73. The heat shrinking serves to securely radially capture the distal portion of the pull member 57 and compress the outer layer 75 of the outer sheath 52 onto the heat shrink resistant support tube 73 to secure them together. Further, the heat shrinking step provides a thorough spreading of the glue layer 61, when done before the glue layer 61 is set, to strongly adhere the distal portion of the pull member 57 to the second layer 69 and the reinforcement layer 59 of the outer sheath 52. The heat shrink resistant support tube 73 is movable axially relative to the inner catheter 3 to allow the outer sheath 52 to be moved relative to the inner catheter 3 and the stent device 4 so as to carry out the process of retracting the outer sheath 52 and deploying the stent device 4.

The inner layer 68 of the outer sheath 52 is heat shrunk at the connecting portion 72 onto a heat shrink resistant portion of the inner catheter 3 at a location proximal of the stent device 4. This provides a connection of the inner layer 68 to the inner catheter 3 sufficiently strong to prevent slippage of the inner layer 68 relative to the stent device 4, yet peelable under normal retraction forces for retracting the outer sheath 52 to allow the outer sheath 52 and the inner catheter 3 to be removed independently of one another after the stent device 4 has been deployed, if this is desirable.

FIG. 5 shows a cross section of the stent device delivery system allowing the circumferential extent of the distal portion of the pull member 57 to be viewed. As can be seen, the pull member 57 comprises a proximal pull wire that has been flattened at the distal portion to provide a low profile portion for fitting between the second layer 69 and the reinforcement layer 75.

In the stent device delivery system 50 of FIGS. 4 and 5, the outer guide sheath 71 and the guide portion 8 of the inner catheter 3 are both made of a slitted tubing for resisting endwise compressive stress and also allowing flexibility for navigating to the target stent site with an outer tubular sleeve layer overlaying the slitted tube.

In each of the delivery systems 1, 30, 50 of the Figs., the inner layer along a portion overlaying the stent device 4 is preferably a cold-drawn polymeric material. One reason for this is that the cold-drawn material is relatively strong as compared to the pre-drawn material. Another reason is that the cold-drawn polymeric material has been found to be conducive to smooth and stick-free rolling in a rolling outer sheath construction. This is discussed in greater detail in WO 2010/076057 and WO 2010/076052, each of which are incorporated by reference in its entirety into this application. There are manufacturing benefits to the use of cold-drawn polymeric material for the outer sheath along a portion overlaying the stent device 4, as will be described below. Thus, preferably the inner layer 68, the second layer 69 and the reinforcement layer 59 are cold-drawn along an axial portion of the outer sheath 52 overlaying the stent device 4. In other words, the distal portion 66 of the outer sheath 52 is made of a cold-drawn polymeric material. The preferred cold-drawn material is polyethylene terephthalate (PET), but other polymeric materials capable of being both cold-drawn and heat-shrunk are useful.

The proximal portion of the outer sheath 52 is heat shrunk onto the heat shrink resistant support tube 73, which thus forms a reduced diameter portion of the outer sheath 52. A transition section 64, therefore, exists between the proximal portion 65 and the distal portion 66 of the outer sheath. The heat-shrunk proximal portion 65 of the outer sheath 52 has been strengthened by this heat treatment, which again contributes to a reduced risk of breakage of the outer sheath at the proximal portion 65. An example heat shrink resistant material for the support tube 73 is polyimide.

In an alternative to that shown in the stent device delivery system 50 of FIGS. 4 and 5, it can be envisaged that the reinforcement layer 59 could be done away with. The distal portion of the pull member 57 could be captured radially between the support tube 73 and the outer layer 69 by heat shrinking the outer layer 69 onto the support tube 73. An adhesive layer could still be used to attach the distal portion of the pull member 57 to the outer layer 69 and the support tube 73. The adhesive layer could also be used to attach the outer layer 69 to the support tube 73. A reinforcement layer could be applied in this alternative construction, but extending just along a portion of the outer layer 69 overlaying the stent device 4 and perhaps also the transition section 54 of the outer sheath 52. In another alternative construction to the stent device delivery system 50 shown in FIGS. 4 and 5, the reinforcement layer 59 may be laminated on the outer layer 69 of the outer sheath 52 along the proximal portion 65 of the outer sheath and not distally further. In another alternative, the reinforcement layer 59 may be laminated to the outer layer 69 along the proximal, heat shrunk portion 65 and the transition section 64, but which does not overlay the stent device 4.

The stent bed 5 in the system 50 is again formed into a tapering profile, which tapers radially inwardly from a distal end to a proximal end. The inner layer 68 is formed to share substantially the same tapering profile so that it has a larger outside diameter at the distal end and a smaller outside diameter at the proximal end and tapers substantially linearly therebetween. The second layer 69 is formed to have a reverse taper, whereby the distal end adjacent the fold-over portion 70 has a smaller diameter than a proximal end at the proximal end of the stent device. The inner and outer layer 68, 69 are formed with this taper in the manner described below, which involves cold-drawing a tube of material along a mandrel having a continuously increasing outside diameter and then folding the tubing material back onto itself to provide two layers of material tapering in reverse directions. This feature of the inner layer 68 and the second layer 69, so as to have a taper in reverse directions, exaggerates a radial gap between the two layers during retraction of the outer sheath 52 to avoid the possibility of the layers 68, 69 catching on one another. Catching of the layers can create increased deployment force, and thus decreased the reliability of successful retraction of the outer sheath 52 from the stent device 4.

In the stent device delivery system 50 of FIGS. 4 and 5, the outer sheath 52 is retracted from the stent device 4 by a rolling mechanism as described with respect to FIG. 4. The pulling member 57 is subjected to a proximal pulling force, which will be transferred to the outer sheath 52 because the distal portion of the pull member 57 is securely captured radially between the support tube 73 and the second layer 69 on one side of the pull member 57 and the reinforcement layer 59 on the other side. Further, the glue layer 61 bolsters the securement of the distal portion of the pull member 57 to the reinforcement layer 59 and the second layer 69. The support tube 73 moves axially with the outer sheath 52 because the outer layer 75 of the outer sheath 52 is heat-shrunk onto the support tube 73. As the outer layer 75 moves proximally, the rolling fold-over portion consumes the inner layer 68 and extends the length of the outer layer 75 so as to progressively uncover the stent device 4 and allow the stent device 4 to expand to a deployed configuration. Once the fold-over portion 70 reaches the connection portion 72, where the inner layer 68 is connected to the inner catheter, further pulling the pull member 57 causes the connection portion 72 to peel away from the inner catheter 3 to disconnect the outer sheath 52 and the inner catheter 3.

In an alternative to the stent device delivery system 50 shown in FIGS. 4 and 5, the pull member 57 could extend further distally so as to at least partly overlay the stent device 4. The pull member 57 would still be laminated radially between the second layer 69 and the reinforcement layer 61. The same proximal portion 65 of the outer sheath 52 would be heat shrunk onto the support tube 73. This would mean that an axial portion of the pull member 57 proximal of a very distal portion would be captured by the heat shrunk portion of the outer sheath 52. In this possible modification to the system 50 shown in FIGS. 4 and 5, a greater axial portion of the pull member would have to be flattened to keep a low profile. The benefits of extending the pull member further towards a distal end of the outer sheath 52 has been discussed above with respect to FIGS. 1 and 2.

The reinforcement layer 59 is provided with a hydrophilic outer layer. This allows low friction delivery of the system 50 to the target tissue site because the outer surface becomes extremely lubricous when it is coated with water, as it would be in the vasculature of a patient. Providing the outermost surface of the outer sheath with a hydrophilic coating is also applicable to the other delivery systems 10, 30 shown in FIGS. 1 to 3 and described above.

A method of manufacture of the stent device delivery systems of FIGS. 4 and 5 is given in the following. The method steps required to provide the stent device delivery system 1 of FIGS. 1 and 2 and the stent delivery device 30 of FIG. 3 will also be subsequently disclosed.

The stent device 4 must first be loaded into a tube of material, which will ultimately form at least part of the outer sheath 52. The stent device 4 is crimped into a reduced diameter configuration using a known crimping machine and transferred into the tube of outer sheath material. The inner catheter 3 having the stent bed 5 mounted thereon is then placed within the lumen of the stent device by simple insertion. In order to engage the stent device with the stent bed 5, the stent device must be further reduced in its radial dimension. To do so, the tube of outer sheath material is cold-drawn along an axial portion where the stent device 4 is located. Necking of the tube of outer sheath material during this process reduces the diameter of the stent device and engages the outer surface of the stent bed 5 with the inner surface of the stent device 4. The cold-drawing process can be performed by hand and is best done by starting from a middle portion of the stent device 4 and pulling one way along the axis of the tube of outer sheath material with one hand and the other way with the other hand until the outside diameter of the stent device 4 can be reduced no more, which signifies strong engagement between the stent bed 5 and the stent device 4. This process is continued along the full length of the stent device 4 to put the stent device 4 into the radially reduced, delivery configuration shown in FIG. 4. This cold-drawing process is described in WO 2009/135934, which is incorporated by reference in its entirety into this application.

A mandrel is then abutted against an end of the stent device 4, being the end that will become the distal end of the stent device. When a stent bed 5 is used having a tapering profile, the distal end can be identified by the end of the stent device 4 overlaying the larger outside diameter end of the stent bed 5. The mandrel is placed within the tubular sheath and continues the profile of the outside diameter of the stent device 4 to give a surface against which an extension portion of the tube of outer sheath material can be cold-drawn. Preferably, the mandrel tapers radially outwardly along its axis from an end in abutment with the stent device 4. The tapering profile of the mandrel has substantially the same gradient as the taper of the stent bed 5. The mandrel begins at the end abutted with the stent device 4 having substantially the same outside diameter as the end of the stent device 4. An extension portion of the tube of outer sheath material is formed by cold-drawing the tube against the mandrel for an axial length of at least the length of the stent device and preferably slightly more to allow for manufacturing tolerance.

A distal end of the tube of outer sheath material has a small cut made in it, where distal is to be understood as in the direction from the stent device 4 to the extension portion. The cut allows the tube of outer sheath material to be folded back upon itself so that the extension portion is reversed back to overlay the portion of the tube of outer sheath material overlaying the stent device 4. A lubricant material may be applied along the tube of outer sheath material before it is folded back onto itself in order to allow the portion that has been folded back onto itself to move more freely relative to the inner layer of material in contact with the stent device 4. These steps have provided a stent device 4 in a radially reduced delivery configuration engaging a stent bed 5. The stent device is held in the delivery configuration by an inner layer 68 of cold-drawn polymeric material engaging an outer surface of the stent device. An outer layer 69 that has been folded back to provide the fold-over portion 70 overlaps the inner layer 68 in the axial direction. The outer layer 69 and the inner layer 68 are tapered in reverse senses by this cold-drawing and folding operation.

In order to make the system 1 shown in FIGS. 1 and 2, a layer of adhesive is applied along the tube of outer sheath material at least along a portion overlaying the stent device 4 and up to where the fold-over portion 12 will be once the folding operation has been carried out. A pull member 7 is placed on the tube of outer sheath material so that it overlays the stent device 4 and extends marginally beyond the stent device 4. The tube of outer sheath material is then folded back onto itself so as to form an outer layer 10 and an inner layer 9 and a fold-over portion 12 connecting them. The outer layer 10 is moved relative to the inner layer 9 until the fold-over portion 12 makes contact with the end of the pull member 7. The outer layer 10 can be rotated back and forth relative to the inner layer 9 to spread the glue layer 11 that is radially between them. The glue layer 11 is then allowed to set or preferably is actively cured by application of UV radiation. In such a preferable case, the adhesive used is a UV curable adhesive, for example that sold under the trade name Dymax. An outer sheath 2 as shown in FIGS. 1 and 2 is thus formed having an inner layer 9, a fold-over portion 12 and an outer layer 10 that are formed into a single laminar structure and having a pull member 7 positioned radially between the two layers and embedded in the glue layer 11 adhering the inner and outer layers 9, 10 together.

Now described are the further steps necessary to form the stent device delivery system 30 shown in FIG. 3, starting from the stage of the manufacturing process for the system 50 of FIGS. 4 and 5 reached in the above description. A further tube of sheath material is inserted into the outer layer proximal of the stent device, which is into the end opposite where the fold-over portion 40 is located. The further tube of outer sheath material forms the reinforcement layer 29. The outer layer 39 and the reinforcement layer 29 are overlapped in the axial direction by a distance of about 5 cm. Before the tube of reinforcement layer material is inserted into the proximal portion of the outer layer 39, a glue layer 31 is applied to the end portion of the tube of reinforcement material that will overlap in the axial direction with the proximal portion of the outer layer 39. The tube of reinforcement material is rotated circumferentially so as to spread the glue layer 31 uniformly around the circumference of the outer layer 31.

The remainder of the tube of reinforcement material that is not laminated with the outer layer 39 is cut away. The distal portion of the pull member 37 is inserted into the glue layer 31 until it reaches the distal end of the reinforcement layer 29. The distal portion of the pull member is thus embedded in the glue layer and captured between the reinforcement layer 29 and the outer layer 39. In the preferred embodiment where the glue layer 31 is UV curable, the glue layer 31 is exposed to a UV light source so as to uniformly cure the adhesive. This is a simple to manufacture yet highly effective method of securing the pull member 27 to the outer sheath 34.

Referring back to the manufacture of the stent device delivery system 50 shown in FIGS. 4 and 5, the tip member 6 has a bore in a proximal end to fit over the inner catheter 3. The tip member 6 is fitted to the inner catheter 3 in this manner. Holes extending radially through the tip member 6 communicate with the inner catheter 3. A "dot" of glue is injected into each of these holes to secure the tip member 6 to the inner catheter 3.

The heat resistant support tube 73 is inserted in a proximal end of the outer layer 69 radially inside the outer layer. The support tube 73 is inserted to axially overlap with the outer tube 69 for a length that will form the heat shrunk portion described above. The overlapping proximal portion of the outer layer 69 is then heat shrunk onto the support tube 73. The heat shrunk portion of the outer layer 69 will be about 5 to 10 cm long.

Glue is applied to an outer surface of the outer layer 69 along an axial portion overlaying the stent device 4. A tube of reinforcement layer material is slid over the outer layer 69, substantially up to a proximal end of the outer layer 69, where a distal to proximal direction is in the direction of the stent device 4 to the support tube 73 along the axis of the system 50. Axially sliding the tube of reinforcement layer material in this way will spread the glue axially to the proximal end of the outer layer 69. The tube of reinforcement layer material 59 also is rotated to spread the glue uniformly in the circumferential direction.

The tube of reinforcement layer material is then cold-drawn along an axial portion of the system 50 from a proximal end of the stent device 4 to distal end of the outer layer 69. This serves to compact the distal portion 66 of the system 50 to ensure a reduced profile. Any excess material of the tube of reinforcement layer extending beyond the fold-over portion 70 is cut away. The cold-drawing process also uniformly squeezes the glue by spreading it axially along and circumferentially around the reinforcement layer 59. Any excess glue can be expelled from the distal end of the reinforcement layer 59. This allows a thin layer of glue to remain between the outer layer 69 and the reinforcement layer 59.

The axial portion of the reinforcement layer 59 overlaying the support tube 73 is heat shrunk onto the support tube 73. This and the above mentioned heat shrinking process can be carried out using a thin heat blade at a temperature of 220° C. when a PET reinforcement layer 59 is being used. The heat blade ensures an accurate application of heat where heat shrinking is to be carried out. In particular, the stent device 4 is, because it is made of a temperature based memory material, particularly sensitive to being subjected to such a high temperature. Further, heat shrinking distally of the heat shrink resistant support tube 73 would cause radial contraction in that area, which might block or hinder the process of retraction of the outer sheath 52. Accordingly, it is only the portion of the reinforcement layer 59 and the outer layer 69 overlaying the heat shrink resistant support tube that is subjected to the high temperatures from the heat blade. Before the heat shrink process is carried out, a distal portion of the pull member 57 is inserted into the glue layer 61 and radially between the reinforcement layer 59 and the outer layer 69 so that the reinforcement layer 59, the outer layer 69 and the distal portion of the pull member 57 overlap in the axial direction for a distance of about 5 cm. The heat shrinking process serves to uniformly distribute the glue layer 61 around and along the reinforcement layer 59 and also causes a thorough embedding of the distal portion of the pull member 57 in the glue layer 61.

The stent device delivery system 50 is subjected to ultraviolet light along where the glue layer 61 is present to cure the glue layer 61 and thus complete the lamination of the outer layer 69 and the reinforcement layer 59.

Once the glue is set, the pull member 57 can be attached at a proximal end to a tension meter to determine the working force for retracting the outer sheath 52. Tests have been conducted and a maximum deployment force of below 20 N is consistently and reliably achieved with the stent device delivery system 50. An upper limit for the deployment force of 20 N has been chosen to provide sufficient tolerance to guard against any possibility of failure of the polymeric material used to create the outer sheath 52 from failing. Retraction of the outer sheath 52 is so low that that extremely thin (about 20 μm) polymeric layers of material can be safely used to construct a low profile stent device delivery system. Further, tests on the attachment of pull member to the outer sheath 52 show that the pull member can be subjected to far greater forces than that required to retract the outer sheath 52 before it separates from the outer sheath 52.

What is claimed is:

1. A stent device delivery system, comprising:

a stent device;

an outer sheath comprising a first polymer-based layer, a polymer-based reinforcement layer, and a glue layer disposed between the first layer and the reinforcement layer wherein the outer sheath overlays the stent device in a radially compact, delivery configuration of the stent device, the outer sheath retractable from a distal end of the stent device to a proximal end of the stent device to allow for radial expansion of the stent device to a deployed configuration;

an outer catheter extending distally from a proximal end of the system and ending proximally of the stent device wherein the outer catheter is disposed radially outward of a proximal end of the outer sheath;

an inner catheter extending axially and radially within a lumen of the stent device and providing a stent bed upon which the stent device is located so that a radially inner surface of the stent device engages a radially outer surface of the stent bed, wherein the stent bed defines an inwardly tapering profile, narrowing in radius from a distal portion of the stent device to a proximal portion of the stent device; and a pull member for retracting the outer sheath from the stent device, wherein the pull member is embedded in the glue layer, sandwiched between the first layer and reinforcement layer, and a proximal end of the pull member is disposed radially inward of the outer catheter wherein the outer sheath comprises an inner layer contacting an outer surface of the stent device, an outer layer and a fold-over portion connecting the inner layer and the outer layer, so that proximal movement of the outer layer relative to the inner layer causes the fold-over portion to move proximally axially relative to the stent device in a rolling manner and thus enables retraction of the outer sheath.

2. The stent device delivery system of claim 1, wherein the stent bed tapers such that a change in outer diameter of the stent bed divided by axial length over which the change in outside diameter occurs is in the range of 0.0003 to 0.005.

3. The stent device delivery system of claim 2, wherein the stent bed tapers, such that a change in outer diameter of the stent bed divided by axial length over which the change in outside diameter occurs is in the range of 0.0006 to 0.0009.

4. The stent device delivery system of claim 1, wherein the inwardly tapering profile is stepwise.

5. The stent device delivery system of claim 1, wherein the stent bed is axially continuous with respect to the stent device.

6. The stent device delivery system of claim 1, wherein the stent bed is formed by a plurality of axially separated portions, each of the plurality of axially separated portions having a constant outer diameter less than an outer diameter of a distally positioned portion.

7. The stent device delivery system of claim 1, wherein the stent bed is made of a compressible material and the stent device is partially embedded in the stent bed in the radial direction.

8. The stent device delivery system of claim 1, wherein the stent bed is made of a tacky material, which provides a radial as well as an axial holding force on the stent device relative to the inner catheter such that during expansion of the stent device, the stent device peels away from the tacky material of the stent bed.

9. The stent device delivery system of claim 1, wherein the stent bed is formed as a layer on the inner catheter.

10. The stent device delivery system of claim 1, wherein the outer sheath is formed into a tapered profile with the inner layer tapering radially inwardly from the distal portion to the proximal portion of the stent device and the outer layer progressively tapering radially outwardly along an entire length from the distal portion to the proximal portion of the stent device.

11. The stent device delivery system of claim 1, wherein a portion of the outer sheath overlaying the stent device is formed having a tapering profile substantially following the tapering profile of the stent bed.

12. The stent device delivery system of claim 1, wherein the outer sheath is made of a cold drawn polymeric material at least along a portion thereof overlaying the stent device.

13. The stent device delivery system of claim 1, wherein the first polymer-based layer comprises a polyethylene terephthalate.

14. The stent device delivery system of claim 1, wherein the polymer-based reinforcement layer comprises a polyethylene terephthalate.

15. The stent device delivery system of claim 1, wherein the first polymer-based layer and the polymer-based reinforcement layer are directly attached and in contact with the glue layer.

* * * * *